US007297335B2

(12) United States Patent
Rosenblum

(10) Patent No.: US 7,297,335 B2
(45) Date of Patent: Nov. 20, 2007

(54) IMMUNOTOXINS DIRECTED AGAINST CD33 RELATED SURFACE ANTIGENS

(75) Inventor: Michael G. Rosenblum, Sugar Land, TX (US)

(73) Assignee: Research Development Foundation, Carson City, NV (US)

( * ) Notice: Subject to any disclaimer, the term of this patent is extended or adjusted under 35 U.S.C. 154(b) by 572 days.

(21) Appl. No.: 10/386,204

(22) Filed: Mar. 11, 2003

(65) Prior Publication Data

US 2003/0157092 A1 Aug. 21, 2003

Related U.S. Application Data

(60) Division of application No. 09/026,882, filed on Feb. 19, 1998, now Pat. No. 6,599,505, which is a continuation-in-part of application No. 08/702,205, filed on Aug. 23, 1996, now abandoned, which is a continuation of application No. 08/312,558, filed on Sep. 26, 1994, now abandoned, which is a continuation of application No. 07/866,693, filed on Apr. 10, 1992, now abandoned.

(51) Int. Cl.
*A61K 39/395* (2006.01)
(52) U.S. Cl. .............................. 424/134.1; 424/133.1; 424/135.1; 530/388.73; 530/387.3
(58) Field of Classification Search ............. 424/134.1, 424/135.1, 133, 183.1; 530/388.73, 387.3
See application file for complete search history.

(56) References Cited

U.S. PATENT DOCUMENTS

| | | | |
|---|---|---|---|
| 4,816,567 A | 3/1989 | Cabilly et al. ........... 530/387.3 |
| 4,888,415 A | 12/1989 | Lambert et al. ......... 530/391.9 |
| 4,946,778 A | 8/1990 | Ladner et al. ............. 435/69.6 |
| 5,091,513 A | 2/1992 | Huston et al. ........... 530/387.3 |
| 5,098,890 A * | 3/1992 | Gewirtz et al. ............... 514/44 |
| 5,260,203 A | 11/1993 | Ladner et al. ........... 530/387.3 |
| 5,455,030 A | 10/1995 | Ladner et al. ............ 424/135.1 |
| 5,514,554 A | 5/1996 | Bacus ....................... 435/7.23 |
| 5,571,894 A | 11/1996 | Wels et al. ............... 530/387.3 |
| 5,618,920 A | 4/1997 | Robinson et al. ........ 530/387.1 |
| 5,631,348 A * | 5/1997 | Rosenblum et al. ........ 530/370 |
| 5,677,171 A | 10/1997 | Hudziak et al. ........... 435/7.23 |
| 5,720,954 A | 2/1998 | Hudziak et al. ......... 424/130.1 |
| 5,730,982 A * | 3/1998 | Scheinberg ............... 424/181.1 |
| 5,744,580 A | 4/1998 | Better et al. ................. 530/377 |
| 5,770,195 A | 6/1998 | Hudziak et al. ......... 424/130.1 |
| 5,837,491 A | 11/1998 | Better et al. ............... 435/69.1 |
| 5,977,322 A | 11/1999 | Marks et al. .......... 530/388.85 |
| 6,054,561 A | 4/2000 | Ring ........................ 530/388.1 |
| 6,146,631 A | 11/2000 | Better et al. ............. 424/183.1 |
| 6,165,464 A | 12/2000 | Hudziak et al. ......... 424/142.1 |
| 6,204,023 B1 | 3/2001 | Robinson et al. .......... 435/71.3 |
| 6,331,415 B1 | 12/2001 | Cabilly et al. ............. 435/69.6 |
| 6,387,371 B1 | 5/2002 | Hudziak et al. ......... 424/138.1 |
| 6,399,063 B1 | 6/2002 | Hudziak et al. ......... 424/138.1 |
| 6,512,097 B1 | 1/2003 | Marks et al. ............. 530/391.1 |
| 6,649,742 B1 | 11/2003 | Better et al. ............. 530/387.3 |

FOREIGN PATENT DOCUMENTS

| | | |
|---|---|---|
| EP | 0350230 | 1/1990 |
| WO | WO 91/09058 | 6/1991 |
| WO | WO 93/20848 | 10/1993 |

OTHER PUBLICATIONS

Tanimoto et al Leukemia vol. 3 p. 339 (1989).*
Scheinberg et al Leukemia vol. 3 p. 440 (1989).*
Thrope et al Immunological Reviews vol. 62 p. 119 (1982).*
Andrews et al., "Myeloid-associated differentiation antigens on stem cells and their progeny identified by monoclonal antibodies," *Blood*, 62:124-132, 1983.
Burgess et al., "Possible dissociation of the heparin-binding and mitogenic activities of heparin-binding (acidic fibroblast) growth factor-1 from its receptor-binding activities by site-directed mutagenesis of a signal lysine residue," *J. Cell. Biol.*, 111:2129-2138, 1990.
Chaudhary et al., "A recombinant single-chain immunotoxin composed of anti-Tac variable regions and a truncated diphtheris toxin," *Proc. Natl. Acad. Sci. USA*, 87:9491-9494, 1990.
Co et al., "Chimeric and humanized antibodies with specificity for the CD33 antigen," *J. Immunol.*, 148:1149-1154, 1992.
Cunningham et al., "Antibody engineering-how to be human," *Trends Biotechnol.*, 10:112-113, 1992.
Engert et at ., "Resistance of myeloid leukaemia cell lines to ricin A-chain immunotoxins," *Leuk. Res.*, 15(11):1079-1086, 1991.
Gillies et al., "Antigen binding and biological activities of engineered mutant chimeric antibodies with human tumor specificities," *Hum. Antibodies Hybridomas.*, 1:47-57, 1990.
Houghton and Scheinberg, "Monoclonal antibodies: potential applications to the treatment of cancer," *Semin. Oncol.*, 13(2):165-179, 1986.
La Russa et al., "Effects of anti-CD33 blocked ricin immunotoxin on the capacity of CD34+ Human marrow cells to establish in vitro hematoplesis in long-term marrow cultures," *Exp. Hematol.*, 20:442-448, 1992.
Lambert et al., "An immunotoxinprepared with blocked ricin: a natural plant toxin adapted for therapeutic use," *Cancer Res.*, 51:6236-6242, 1991.
Lazar et al., "Transforming growth factor alpha: mutation of aspartic acid 47 and leucine 48 results in different biological activities," *Mol. Cell. Biol.*, 8:1247-1252, 1988.

(Continued)

*Primary Examiner*—Sheela J. Huff
(74) *Attorney, Agent, or Firm*—Fulbright & Jaworski L.L.P.

(57) ABSTRACT

The present invention provides novel immunotoxins and methods of treating neoplastic diseases. These immunotoxins are comprised of a conjugation of an antigen binding region exhibiting binding specificity for the CD33 protein and a cell growth modulator. The immunotoxins of the present invention specifically and selectively kill tumor cells that are characterized by the expression of CD33 antigen. Thus, the novel immunotoxins would be useful in treating human leukemias, both acute and chronic, and other myelodysplastic syndromes.

16 Claims, 16 Drawing Sheets

OTHER PUBLICATIONS

Maier et al., "Requirements for the internalization of a murine monoclonal antibody directed against the HER-2/neu gene product c-erbB-2." *Cancer Res.* 51:5361-5369, 1991.

Milenic et al., "Construction, binding properties, metabolism, and tumor targeting of a single-chain Fv derived from the pancarcinoma monoclonal antibody CC49," *Cancer Res.*, 51:6363-6371, 1991.

Morrison et al., "Chimeric human antibody molecules: mouse antigen-binding domains with human constant region domains," *Proc. Natl. Acad. Sci. USA*, 81:6851-6855, 1984.

Ozawa et al., "Selective killing of squamous carcinoma cells by an immunotoxin that recognizes the EGF receptor," *Int. J. Cancer*, 43(1):152-157, 1989.

Queen et al., "A humanized antibody that binds to the interleukin 2 receptor," *Proc. Natl. Acad. Sci. USA* , 86:10029-10033, 1989.

Reichmann et al., "Reshaping human antibodies for therapy," *Nature*, 332:323-327, 1988.

Roy et al., "Anti-MY9-blocked-ricin: an immunotoxin for selective targeting of acute myeloid leukemia cells," *Blood*, 77(11):2404-2412.

Scheinberg et al., "Monoclonal antibody M195: a diagnostic marker for acute myelogenous leukemia," *Leukemia*, 3:440-445, 1989.

Scheinberg et al., "A phase I Trial of monoclonal antibody M195 in acute myelogenous leukemia: specific bone marrow targeting and internalization of radionuclide," *J. Clin. Oncol.*, 9:478-490, 1991.

Scheinberg et al., "Humanized and mouse anti-CD33-gelonin immunitoxins for myeloid luekemias," *Proceedings of the American Association for Cancer Research*, 33:346, Mar. 1992.

Scott et al., "An immunotoxin composed of a monoclonal antitransferrin receptor antibody linked by a disulfide bond to the ribosome-inactivating protein gelonin: potent in vitro and in vivo effects against human tumors," *J. Natl. Cancer Inst.*, 79:1163-1172, 1987.

Sivam et al., "Immunotoxins to a human melanoma-associated antigen: comparison of gelonin with ricin and other A chain conjugates," *Cancer Res.*, 47:3169-3173, 1987.

Stripe and Barbieri, "Ribosome-inactivating proteins up to date," *FEBS Lett.*, 195:1-8, 1986.

Stripe et al., "Gelonin, a new inhibitor of protein synthesis, nontoxic to intact cells. Isolation, characterization, and prepared of cytotoxic complexes with concanavalin A," *J. Biol. Chem.*, 255:6947-6953, 1980.

Tanimoto et al., "Restricted expression of an early myeloid and monocytic cell surface antigen defined by monoclonal antibody M195," *Leukemia*, 3:339-348, 1989.

Tao and Morrison, "Studies aglycosylated chimeric mouse-human IgG. Role of carbohydrate in the structure and effector functions mediated by the human IgG constant region," *J. Immunol.*, 143:2595-2601, 1989.

Tecce et al., "Production and characterazation of immunotoxins to distinct epitopes of the extracellular domain of the HER-2 gp185," *Anticancer Res.*, 10:1454, abstract 329, 1990.

Thorpe and Ross, "The preperations and cytotoxic properties of antibody-toxin conjugates," *Immunol. Rev.*, 62:119-158, 1982.

Thorpe et al., "New coupling agents for the synthesis of immunotoxins containing a hindered disulfide bond with improved stability in vivo," *Cancer Res.*, 47:5924-5931, 1987.

Waldmann, "Monoclonal antibodies in diagnosis and therapy," *Science*, 252:1657-1662, 1991.

* cited by examiner

Antibody Concentration (ug/ml)

IMMUNOTOXINS DIRECTED AGAINST CD33 RELATED SURFACE ANTIGENS

PRIORITY APPLICATIONS

This application is a divisional of U.S. Ser. No. 09/026,882 filed Feb. 19, 1998, now U.S. Pat. No. 6,599,505 which is a continuation-in-part application of U.S. Ser. No. 08/702,205 filed Aug. 23, 1996, now abandoned, which is a file wrapper continuation of U.S. Ser. No. 08/312,558 filed Sep. 26, 1994, now abandoned, which is a file wrapper continuation of U.S. Ser. No. 07/866,693 filed Apr. 10, 1992, now (abandoned).

FEDERAL FUNDING LEGEND

This invention was produced in part using funds obtained through grants PO1CA33049 and RO1CA55349 from the National Institutes of Health. Consequently, the federal government has certain rights in this invention.

BACKGROUND OF THE INVENTION

1. Field of the Invention

The present invention relates generally to the field of treatment of neoplastic disease. More specifically, the present invention relates to novel immunoconjugates and their use in the treatment of neoplastic disease. Even more particularly, the present invention relates to novel immunoconjugates cytotoxic to leukemia cells characterized by expression of the CD33 antigen.

2. Description of the Related Art

Neoplastic disease is one of the leading causes of mortality and morbidity in the Western World. All neoplastic diseases or "cancers" share at least one characteristic, i.e., the involvement of defects in the cellular growth regulatory process. Antigens located on the surface of cancer cells have been useful in distinguishing lymphoid from non-lymphoid leukemias, subtyping of acute myelogenous leukemia, predicting therapeutic outcome and in therapy in vivo or via a bone marrow purging ex vivo. Antigens defining acute non-lymphocytic cells also identify normal hematopoietic cells during early stages of their development.

CD33 provides a useful target antigen for therapy of myelogenous leukemias, as it is expressed in the cell-surface of more than 80% of leukemic isolates from patients with myeloid leukemia with an average density of 10,000 sites/cell. In addition, rapid internalization occurs upon binding of mAb to CD33 both in vitro and in vivo. CD33 antigen is a 67 kilodalton glycoprotein found on normal colony forming unit granulocyte-monocyte (CFU-GM), on a fraction of burst-forming unit-erythroid (BFU-E and CFU-granulocyte, erythroid, monocyte, megakaryocyte) CFU-GEMM, and absent from normal pluripotent stem cells.

Antibodies are proteins normally produced by the immune system of an animal in response to antigenic determinants. Antibodies bind to the specific antigen to which they are directed. The development of specific monoclonal antibodies has provided investigators with a possible means of selectively targeting chemotherapeutic agents to cells which overexpress tumor associated antigens.

Immunotoxins are hybrid molecules consisting of a monoclonal antibody covalently linked or genetically fused to a toxin molecule and are thus able to direct potent cytotoxicity to particular cells. Immunotoxins have several possible advantages over conventional anti-neoplastic agents including selectivity for tumor cells and potential delivery of extremely potent toxins. However, obstacles to effective therapeutic use of immunotoxins for cancer include (a) lack of suitable tumor-specific targets that are not also found on other vital non-tumor cells; (b) loss of toxin potency or mAb activity after conjugation; (c) unwanted cytotoxicity to nontarget cells and tissues resulting from nonspecific internalization of the immunotoxin; (d) immunogenicity of the immunotoxin; and (e) pharmacological inability to target tumor sites adequately.

Currently, no immunotoxin exists that meet the above-mentioned criteria for an effective immunotoxin to treat acute non-lymphoid leukemic cells and acute myelogenous leukemic cells. Thus, there continues to exist a great need and desire in this art for compounds and methods of selectively killing leukemia cells. The present invention fulfills this long-standing need and desire in the art.

SUMMARY OF THE INVENTION

The present invention provides a composition comprising a conjugate of an antigen binding region exhibiting binding specificity for the CD33 protein and gelonin, a cell growth modulator derived from plants. Such a composition acts as an immunotoxin to specifically kill tumor cells characterized by the expression of the CD33 protein.

Thus, in one embodiment of the present invention, there is provided a composition comprising a conjugate of an antigen binding region exhibiting binding specificity for the CD33 protein and gelonin or recombinant gelonin or fragments thereof.

In another embodiment of the present invention, there is provided a method of treating neoplastic disease comprising the administration of a cytocidally effective dose of an immunotoxin of the present invention to an individual in need of such treatment.

And yet another embodiment of the present invention, there is provided a method of killing tumor cells in bone marrow comprising removing bone marrow from an individual having a neoplastic disease, treating the bone marrow with a composition of the present invention and infusing the treated bone marrow back into the individual. In another embodiment of the present invention there is provided a method of preventing recurrence of neoplastic disease where the disease is characterized by an expression of CD33 protein. The recurrence is prevented by administration of a cytocidally effective treatment of immunotoxins of the present invention.

In still another embodiment of the present invention, there is provided a new composition of matter comprising a fusion protein formed by the fusion of the CD33 antigen binding region and gelonin or recombinant gelonin or fragments thereof.

In further embodiments of the present invention there are provided methods of extending the survival time of a mammal bearing tumor by administration of the immunotoxin of the present invention to this mammal. In yet further embodiments, there are provided a method of retarding the rate of growth of tumors by administering the immunotoxin of the present invention. Still further, there is provided a pharmaceutical composition comprising an immunotoxin of the present invention.

purified mouse M195; a reaction mixture containing M195 and gelonin; purified M195-gelonin immunotoxin; purified gelonin.

Figure 2:
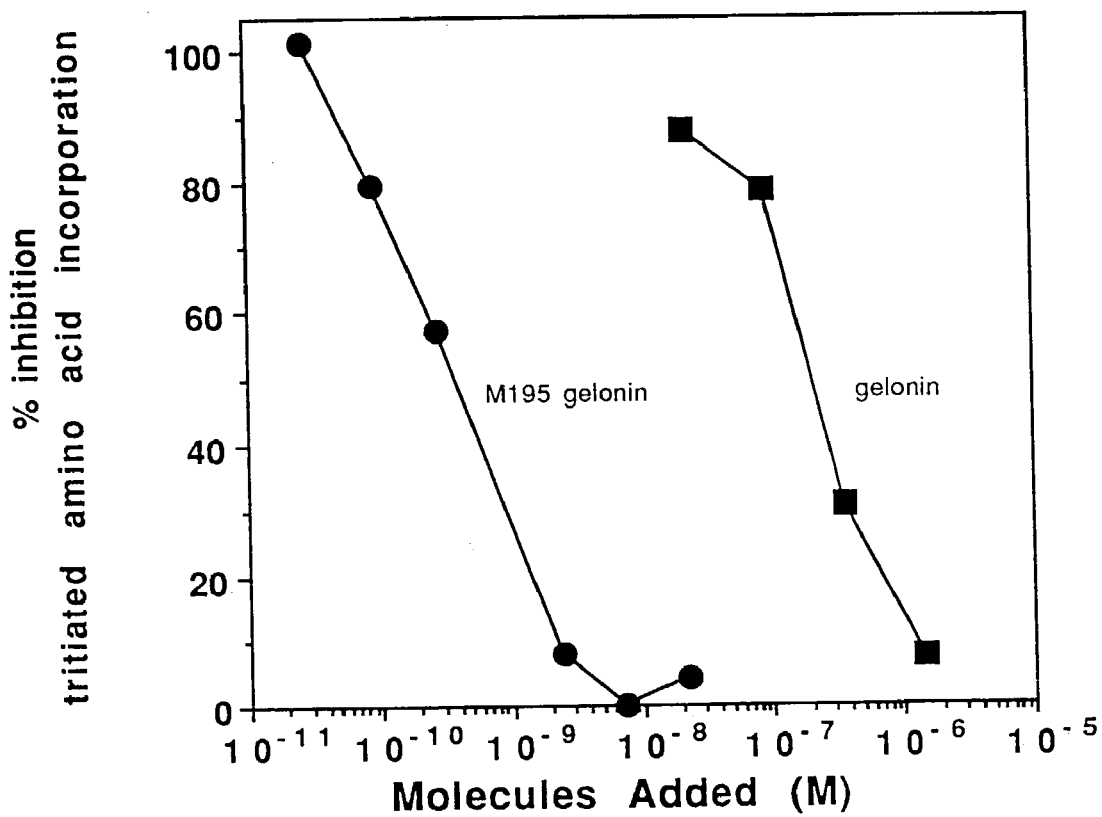

FIG. 2 depicts the inhibition of protein synthesis in live cells by gelonin and the M195 immunotoxin on HL60 cells. HL60 cells at a final concentration of $1\times10^6$ cells/ml were incubated for 3 days at 37° C. in the presence of M195-gelonin immunotoxin (solid circle) or gelonin (filled square). Levels of protein synthesis were determined by 5 hour incorporation of tritiated amino acids into trichloro-acetic-acid-precipitable protein. M195 immunotoxin final concentrations ranged from 5 ng/ml to 4 µg/ml. Gelonin final concentration ranged from 0.5 µg/ml to 50 µg/ml. The data are representative of four experiments.

Figure 3:
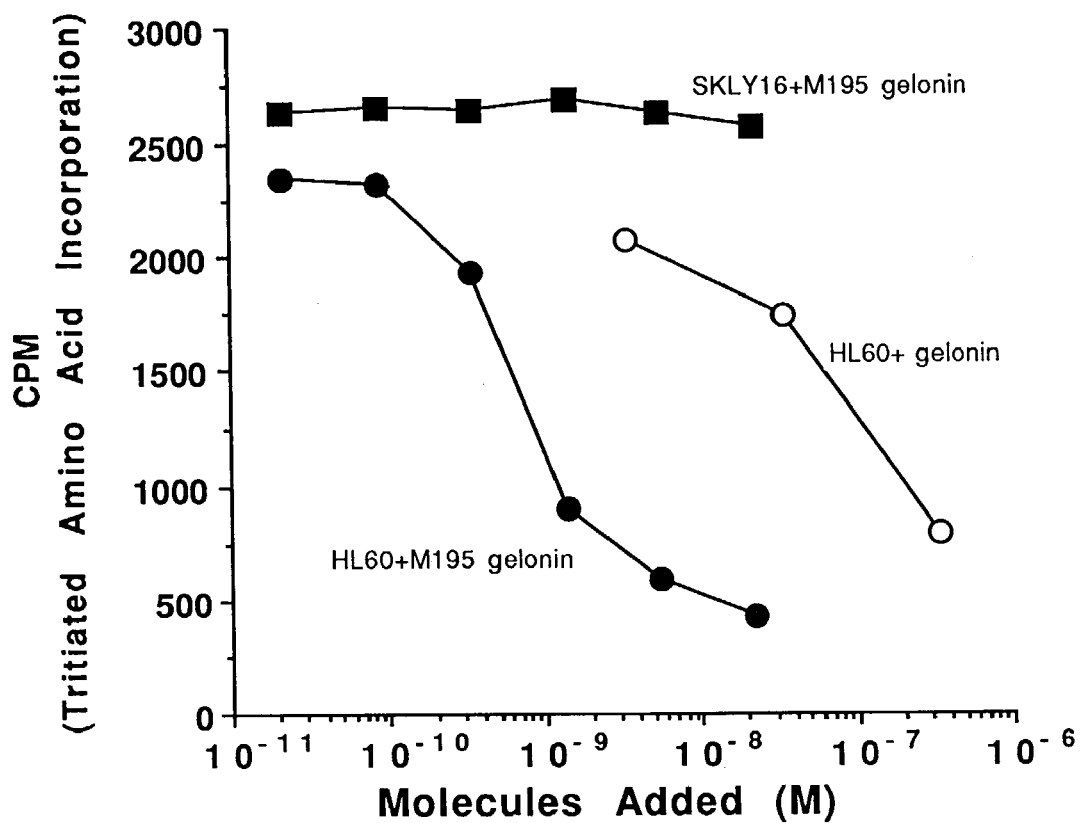

FIG. 3 demonstrates the inhibition of protein synthesis by gelonin and M195 gelonin on SKLY16 and HL60 cell lines. HL60 or SKLY16 cells at a final concentration of $5\times10^5$ cells/ml were incubated for three days at 37° C. in the presence of either gelonin alone or the M195-gelonin immunotoxin. Final concentrations of M195-gelonin immunotoxin ranged from 4 mg/ml to 15.2 pg/ml. Gelonin final concentrations ranged from 10 mg/ml to 0.1 mg/ml. Levels of protein synthesis were determined by a 5 hour incorporation of tritiated amino acids into trichloroacetic acid precipitable protein.

Figure 4:
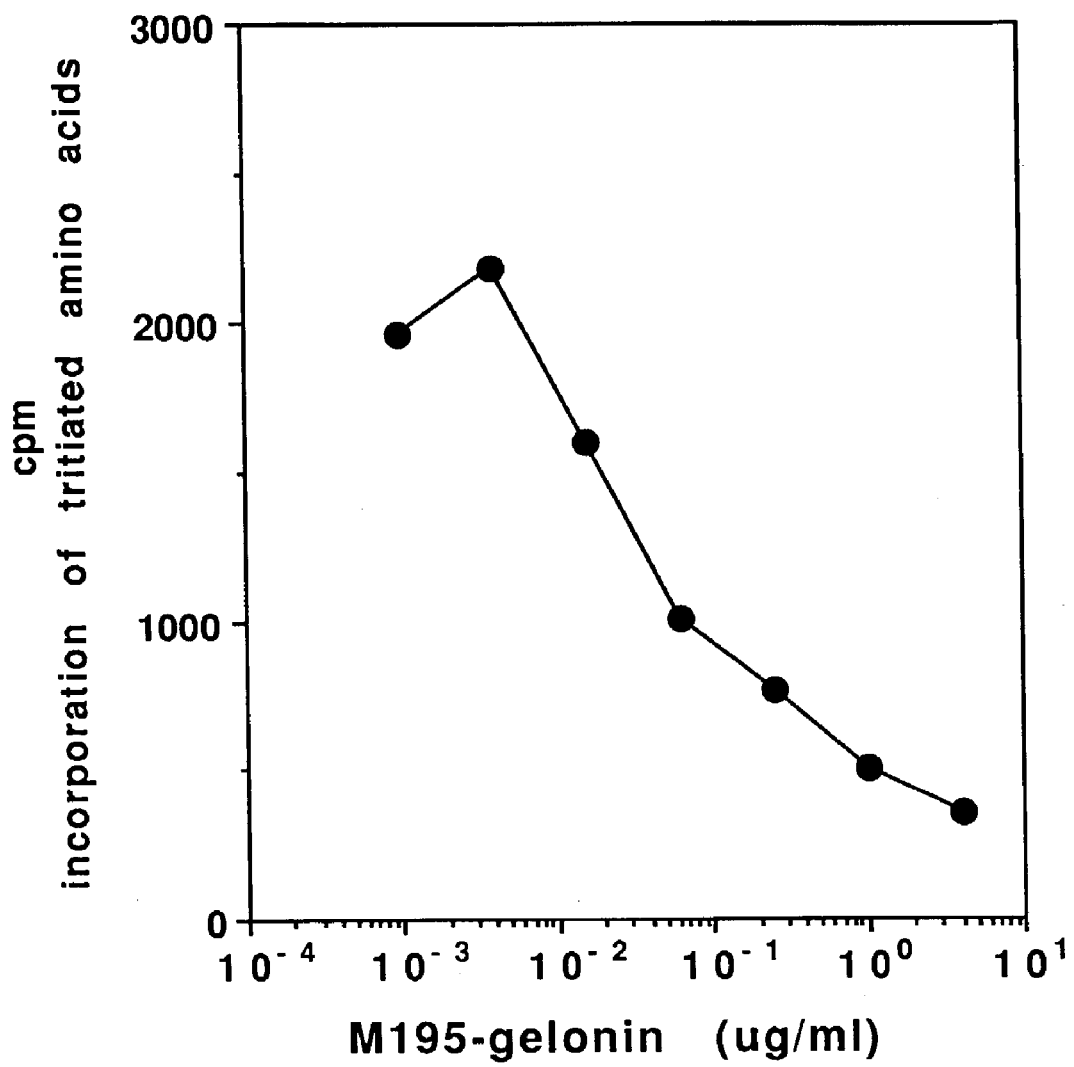

FIG. 4 illustrates the inhibition of protein synthesis by a three day incubation of M195 immunotoxin with HL60. HL60 cells at a final concentration of $1\times10^6$ were incubated for three days at 37° C. in the presence of the M195-gelonin immunotoxin. The final concentration of the immunotoxin ranged from 4 mg/ml to 0.9 ng/ml. Levels of protein synthesis were determined by a 5 hour incorporation of tritiated amino acids into trichloroacetic acid precipitable protein.

Figure 5:
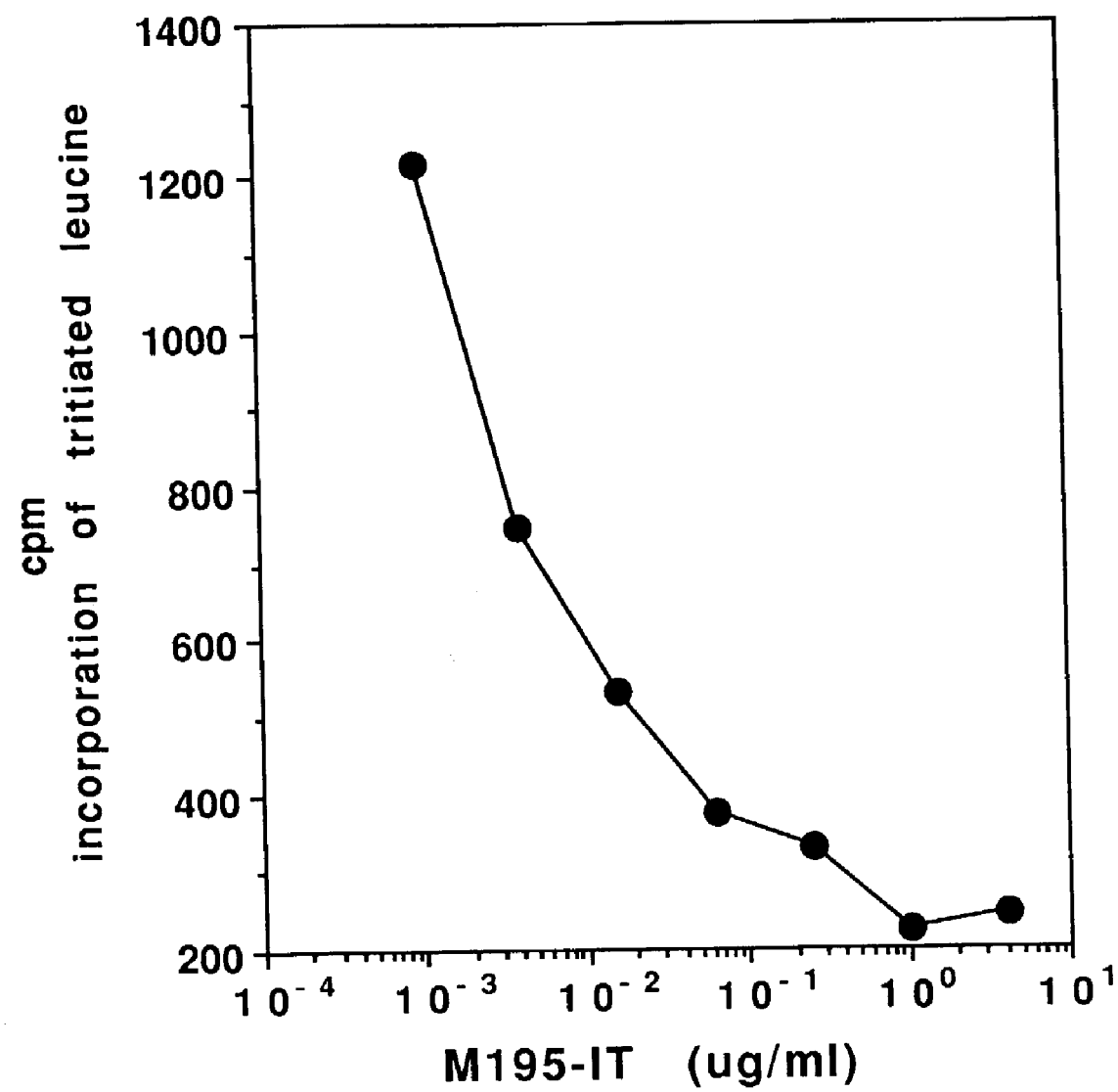

FIG. 5 depicts the inhibition of protein synthesis by a five day incubation of M195-IT on HL60 cells. HL60 cells at a final concentration of $1\times10^6$ were incubated for five days at 37° C. in the presence of the M195-gelonin immunotoxin. The final concentration of the immunotoxin ranged from 4 mg/ml to 0.9 ng/ml. Levels of protein synthesis were determined by a five hour incorporation of tritiated amino acids into trichloroacetic acid precipitable protein.

Figure 6A:
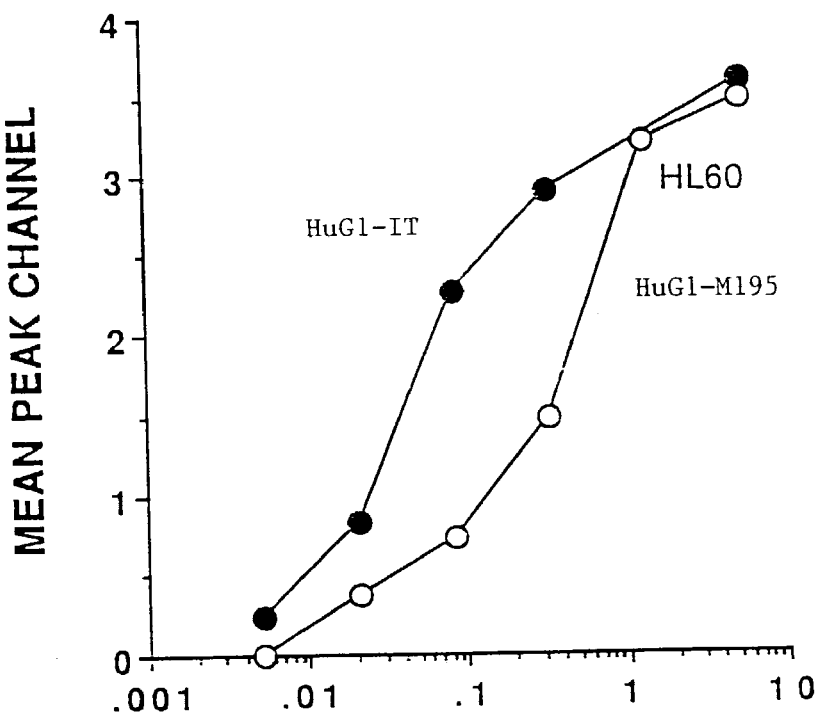
Figure 6B:
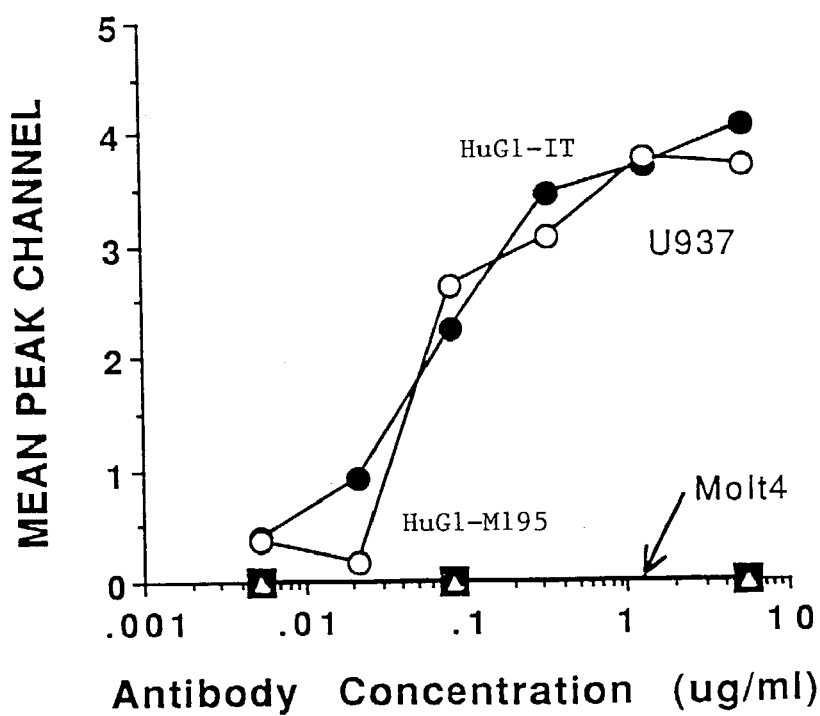

FIGS. 6A–6B show the binding titer and specificity of HuM195-gelonin immunotoxin on cell lines. HL60, U937 or Molt4 cells at a concentration of $1.5\times10^6$ cells/mi were incubated on ice for 1 hour with either HuM195 or MuM195-gelonin at a final concentration range of 0.08 to 10 µg/ml. Mean peak fluorescence intensity (y-axis) versus mAb or immunotoxin (IT) concentration (x-axis) was measured using an EPICS Profile flow cytometer. FIG. 6A shows HL60 binding by HuM195-gelonin immunotoxin (•) or by HuM195 alone (o). FIG. 6B shows U937 binding by HuM195-gelonin immunotoxin (•) or by HuM195 alone (o); Molt4 binding by HuM195-gelonin immunotoxin (filled square) or by HuM195 alone(Δ).

Figure 7:
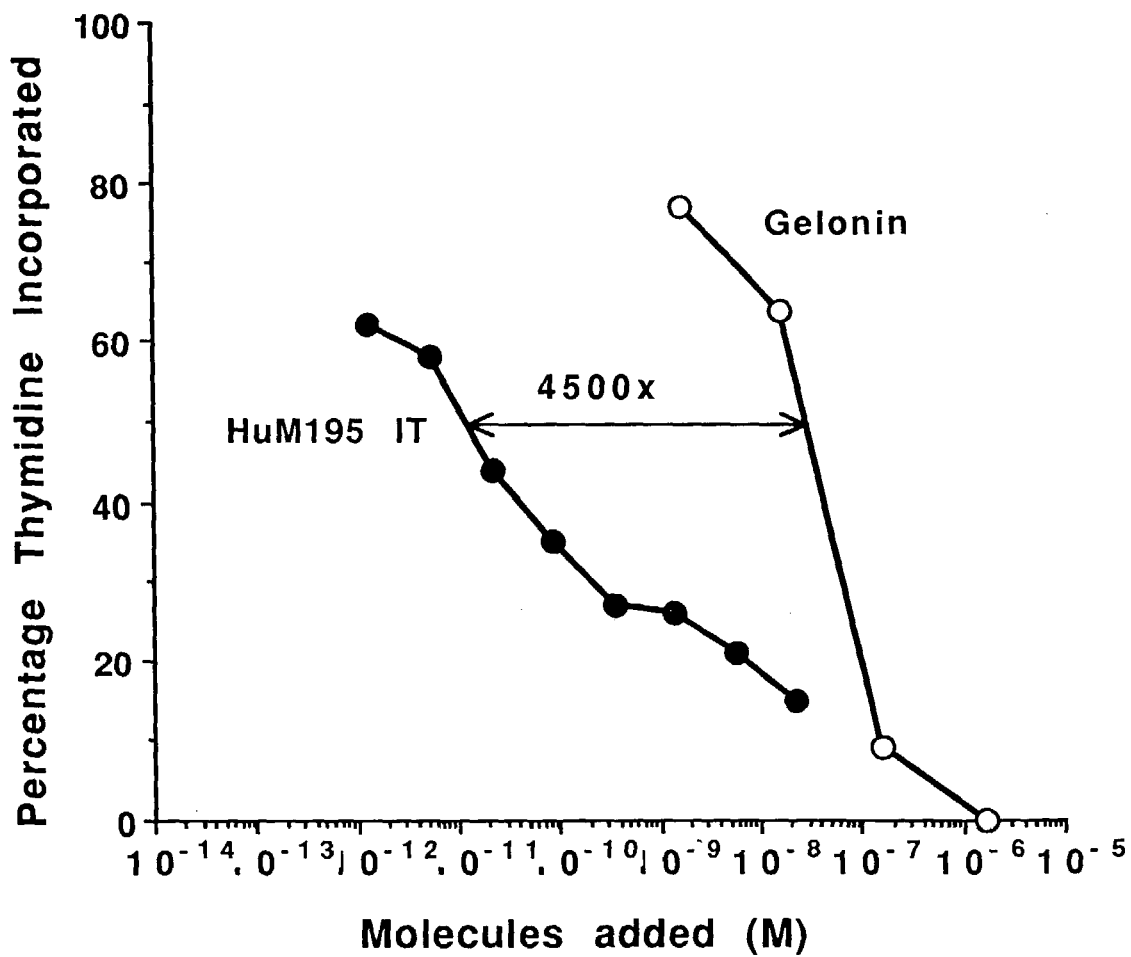

FIG. 7 illustrates the inhibition of DNA synthesis in live cells by gelonin and HuM195-gelomn immunotoxin on HL60 cells. HL60 cells at a final concentration of $3\times10^4$ cells/ml were incubated for 5 days at 37° C. in the presence of HuM195-gelonin immunotoxin (•) or gelonin alone (o). Levels of DNA synthesis were determined by 5 hour incorporation of tritiated thymidine. HuM195-gelonin immunotoxin final concentrations ranged from 0.2 ng/ml to 4 µg/ml. Gelonin final concentration ranged form 0.5 µg/ml to 50 µg/ml. The data are representative of five experiments.

Figure 8:
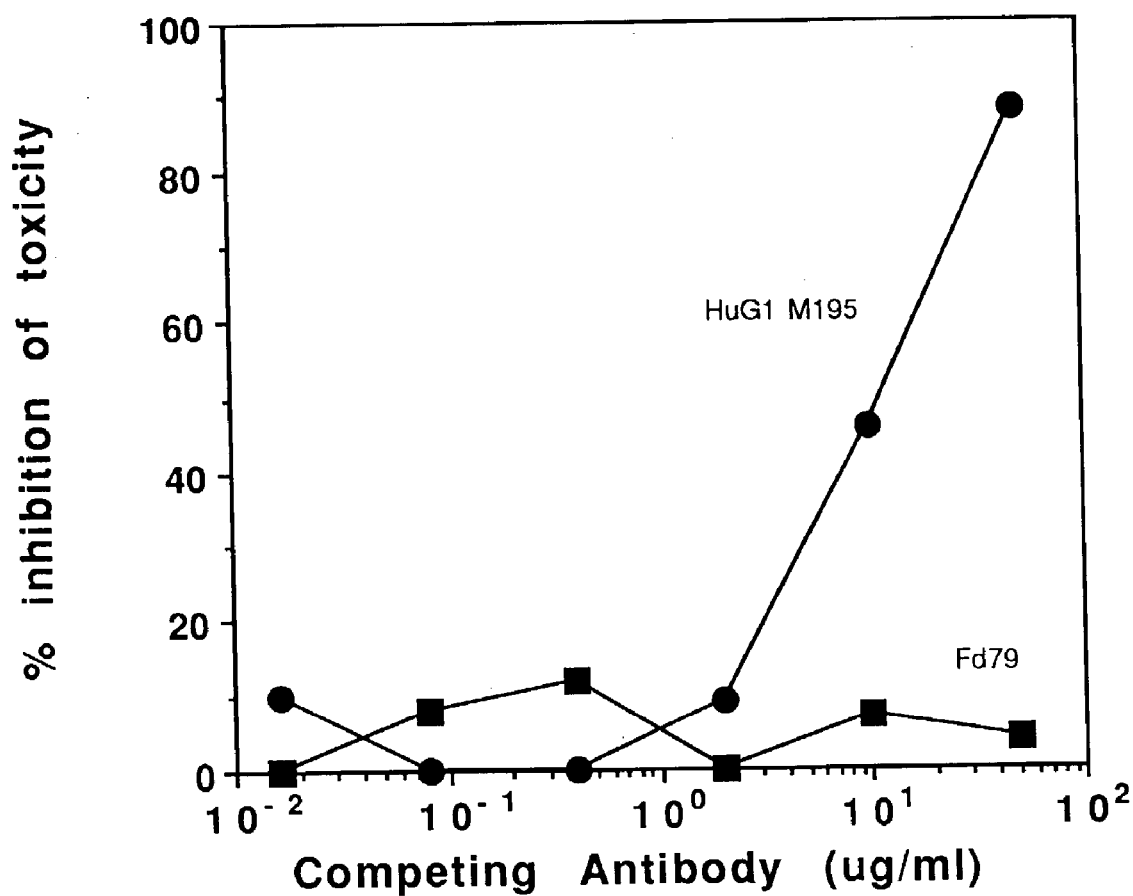

FIG. 8 depicts the competition between the HuM195-gelonin immunotoxin, HuM195 alone or FD79 (an isotype matched control antibody).

Figure 9A:
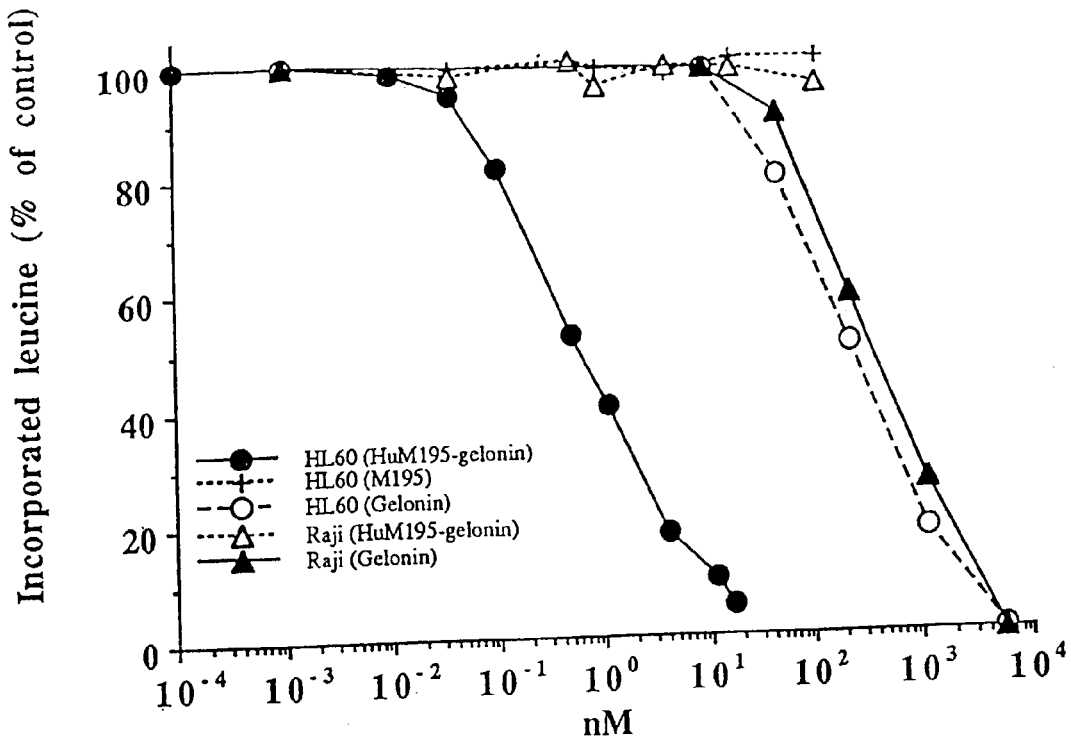
Figure 9B:
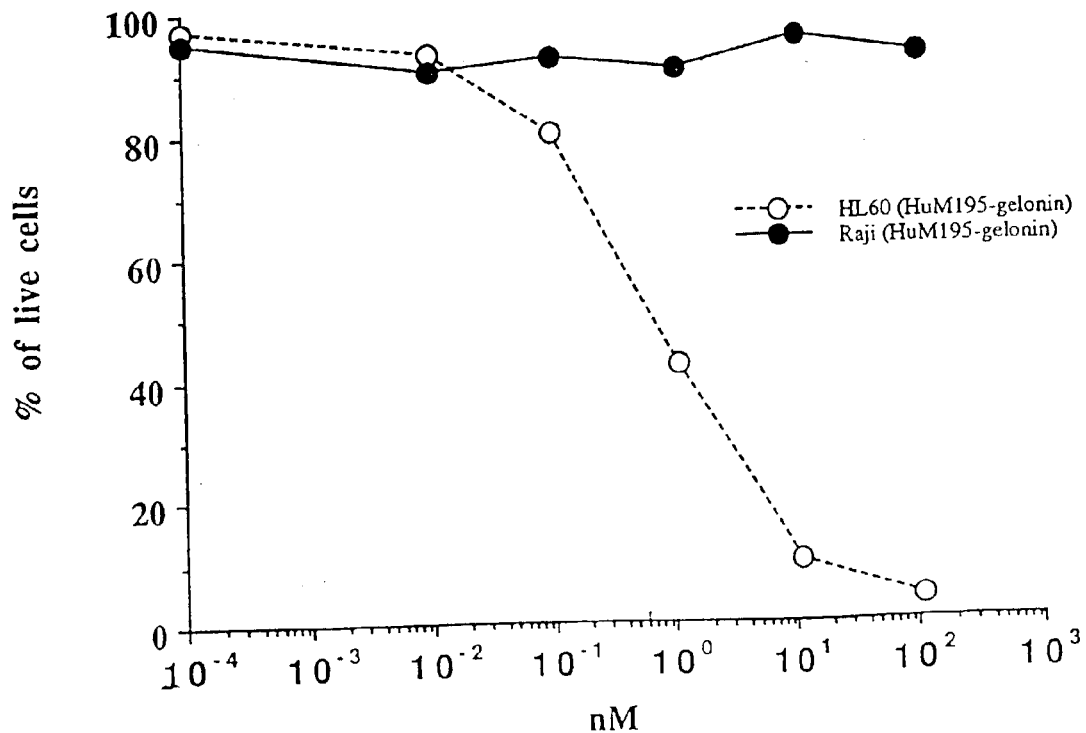

FIGS. 9A–9B show the cytotoxicity and inhibition of protein synthesis in HL60 or RAJI cells by recombinant gelonin (rGel), HuM195 or the HuM195-rGel immunotoxin. FIG. 9A shows the inhibition of protein synthesis in HL60 or RAJI cells by rGel, HuM195 and HuM195-rGel. HL60 or RAJI cells at a final concentration of $10^5$ cells/ml were incubated 3 days at 37° C. in the presence of HuM195-rGel, rGel or HuM195. Levels of protein synthesis were determined by 5 hour incorporation of tritiated leucine into trichloroacetic acid precipitable protein. The treatment is shown in parenthesis. FIG. 9B shows cell viability determined by typan blue exclusion. HL60 or RAJI cells at a final concentration of $10^5$ cells/ml were incubated 3 days at 37° C. in the presence of HuM15-rGel. Typan blue was added and live and dead cells were counted under the microscope.

Figure 10:
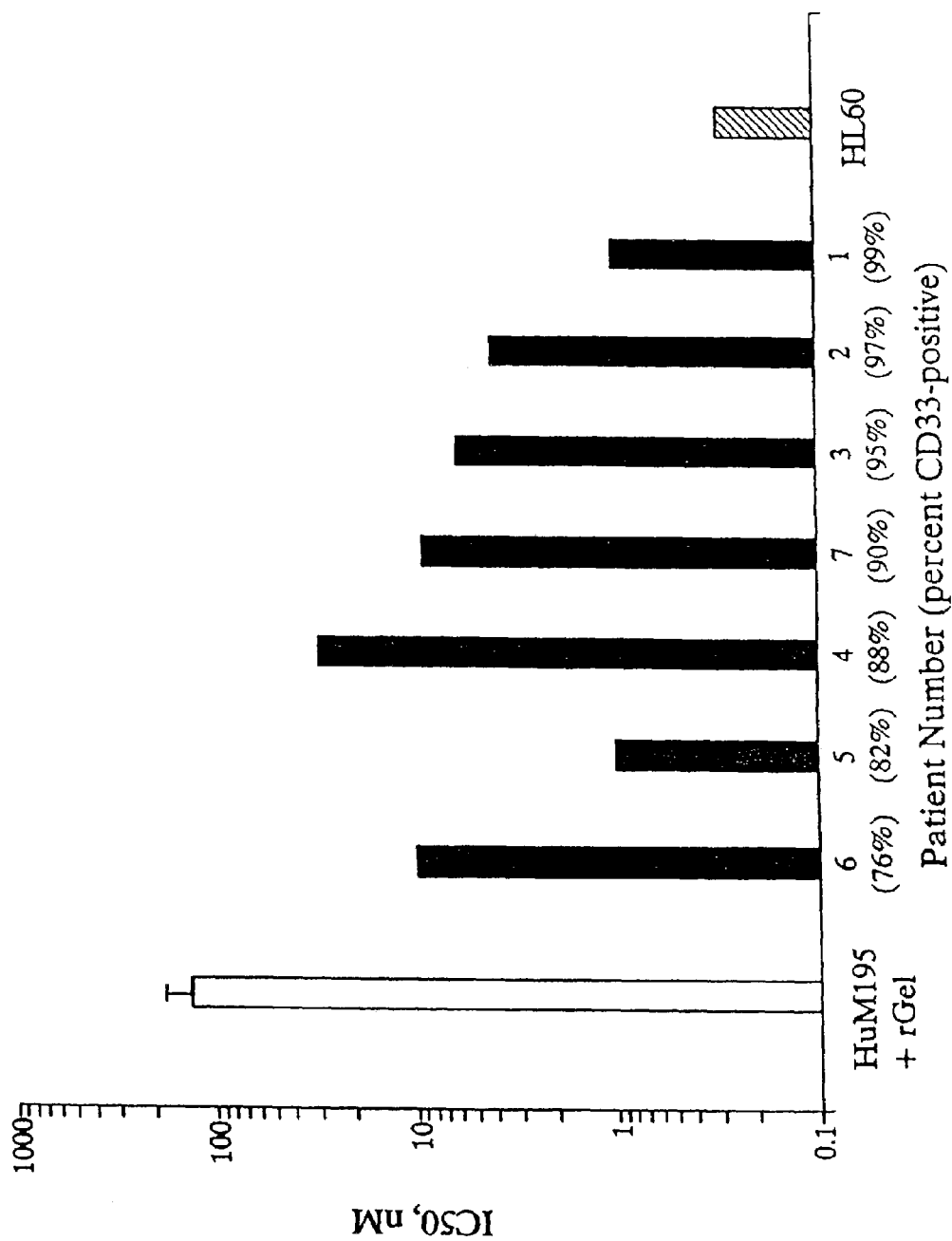

FIG. 10 shows the $IC_{50}$ of HuM195-rGel for blast cells from 7 patients versus percent of cells positive for CD33 by FACS. To establish $IC_{50}$, cells were incubated with the immunotoxin for 24 hours, washed, plated and colonies counted after 5 to 7 days. $IC_{50}$ was estimated from the dose-response curves, which were linear in the range of $IC_{50}$ when plotted on a log/log scale. The open bar shows the mean and standard deviation of $IC_{50}$ obtained with 3 patient samples incubated with equimolar HuM195 and free rGel. The hatched bar shows the $IC_{50}$ for HL60, which is 100% CD33 positive.

Figure 11:
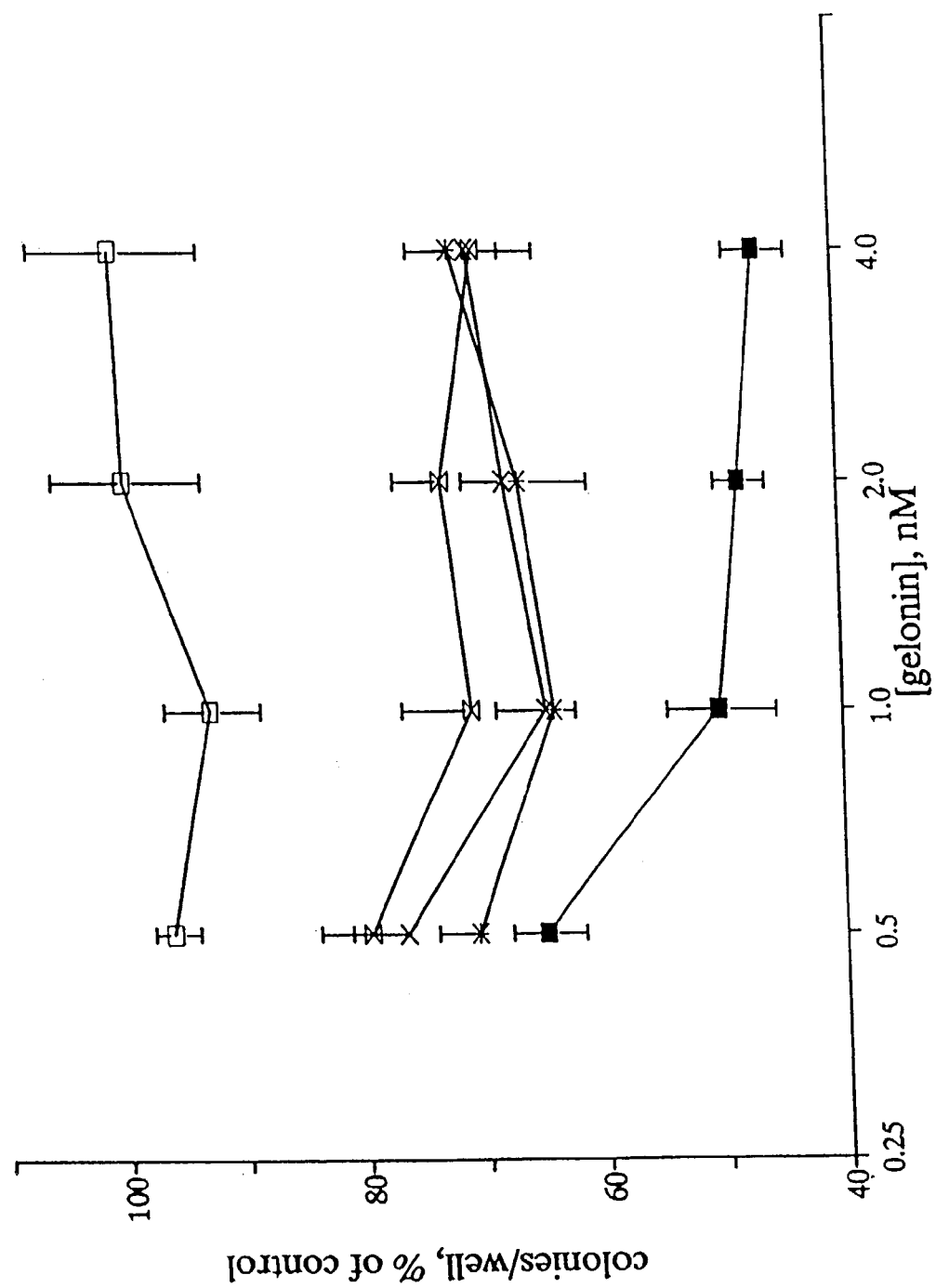

FIG. 11 shows the effect of prolonged exposure on dose-response of OCI/AML5 to the immunotoxin. Cells were incubated with the immunotoxin at 0, 0.5, 1, 2 or 4 nM for 48 hours, washed and plated. Cells surviving 4 nM immunotoxin at 48 hours were collected, washed and resuspended with different concentrations of immunotoxin, and this was repeated at 96 and 120 hours. Concentration curves are shown for OCI/AML5 incubated 48 hours with unconjugated HuM195 and rGel. (open square); immunotoxin without pretreatment (filled square); and immunotoxin following pretreatment with 4 nM immunotoxin for 48 hours (*), 96 hours (X) or 120 hours (X̲). Mean and SEM of quadruplicate wells is shown.

Figure 12A:
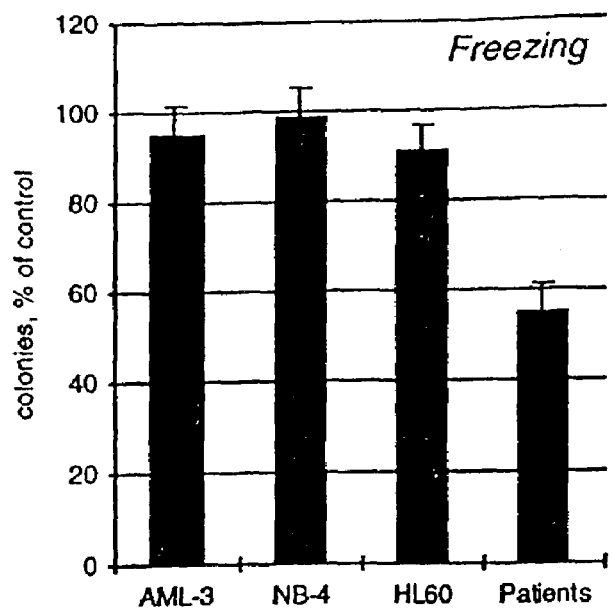
Figure 12B:
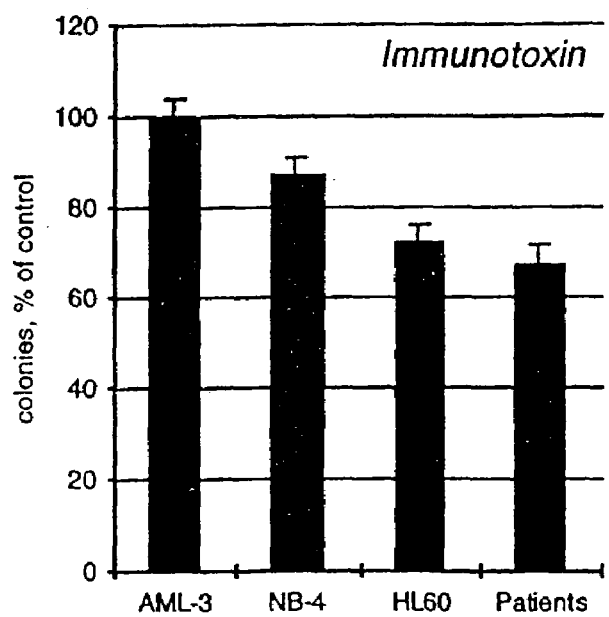
Figure 12C:
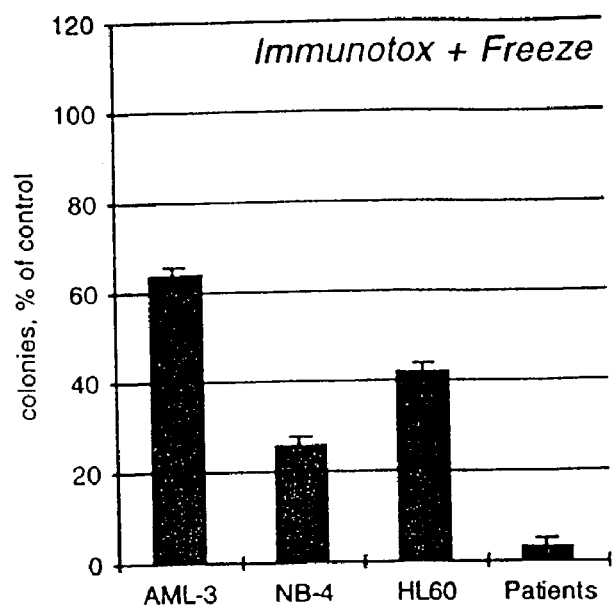

FIGS. 12A–12C show the enhanced effect of the immunotoxin when combined with cryopreservation. The AML cell lines OCI/AML3 (CD33neg), NB4 (CD33pos), HL60 (CD33pos) or patient samples, all CD33 positive, were plated after freeze/thaw alone (A), 1 nM immunotoxin for 24 hours (B), or immunotoxin followed by freeze/thaw (C). Mean colony number was determined from 4 replicate wells and is expressed as percent of control.

Figure 13:
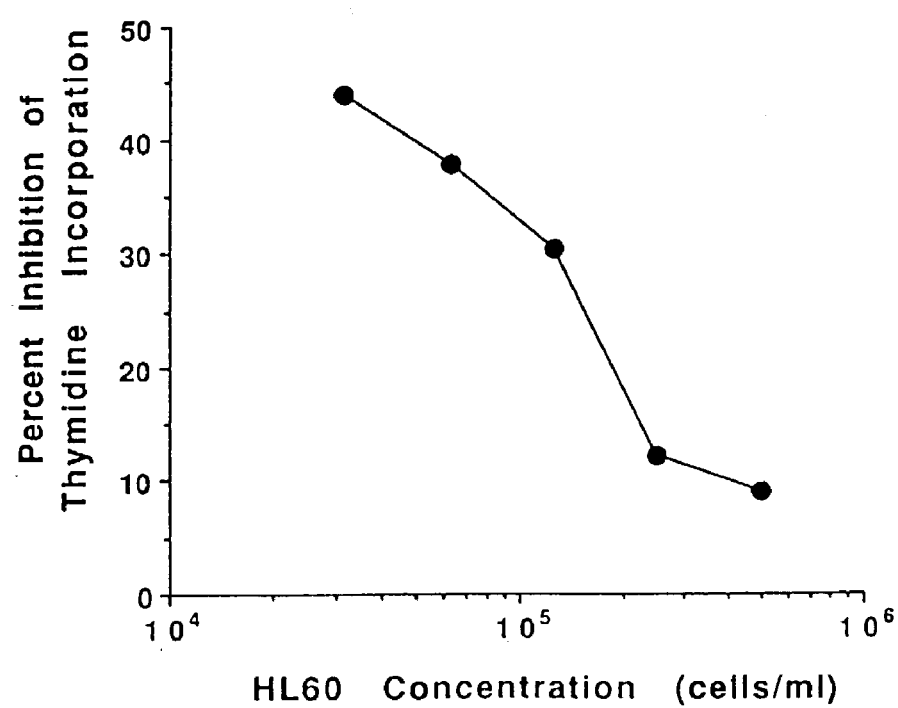

FIG. 13 shows the effect of HL60 concentration upon efficacy of HuM195-gelonin immunotoxin. HL60 cells at a final concentration of $3.125\times10^4$–$5\times10^5$ cells/ml were incubated for 5 days at 37° C. with or without the immunotoxin at a final concentration of 2 µg/ml. DNA synthesis was determined by 5 hour incubation with tritiated thymidine. Percentage inhibition was determined in comparison to control wells without the immunotoxin. The data are representative of 3 experiments.

Figure 14:
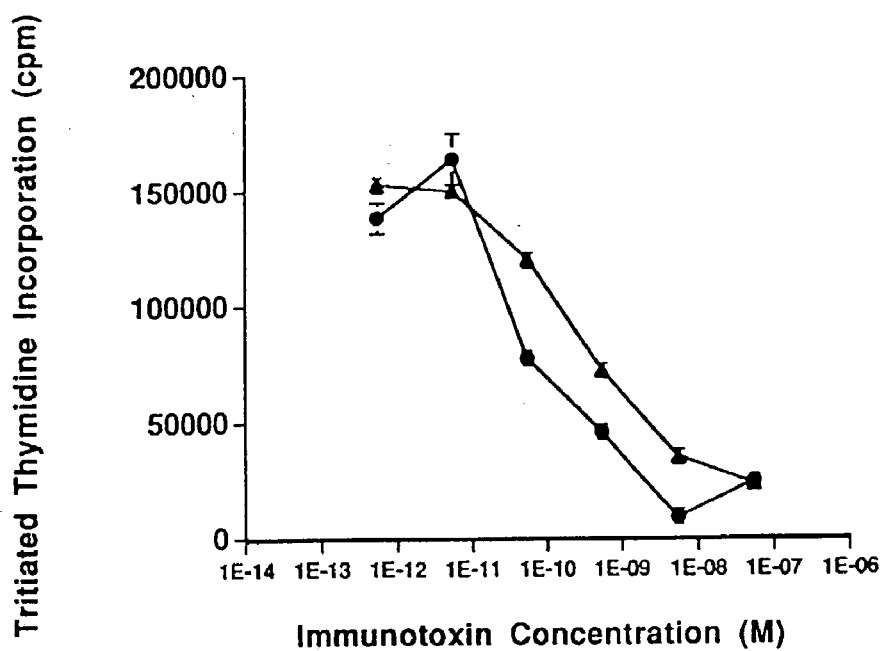

FIG. 14 shows the cytotoxicity of HuM195-gelonin immunotoxin on HL60 in the presence of excess irradiated bone marrow. HL60 cells at a final concentration of $6.67\times10^4$ cells/ml in the presence (filled triangle) or absence (filled circle) of normal irradiated bone marrow at $1\times10^6$ cells/ml were incubated for 6 days at 37° C. in the presence of HuM195-gelonin immunotoxin at a final concentration of 100 pg/ml to 10 µg/ml. Levels of DNA synthesis were determined by measuring 5 hour tritiated thymidine incorporation. The data are representative of two experiments.

Figure 15:
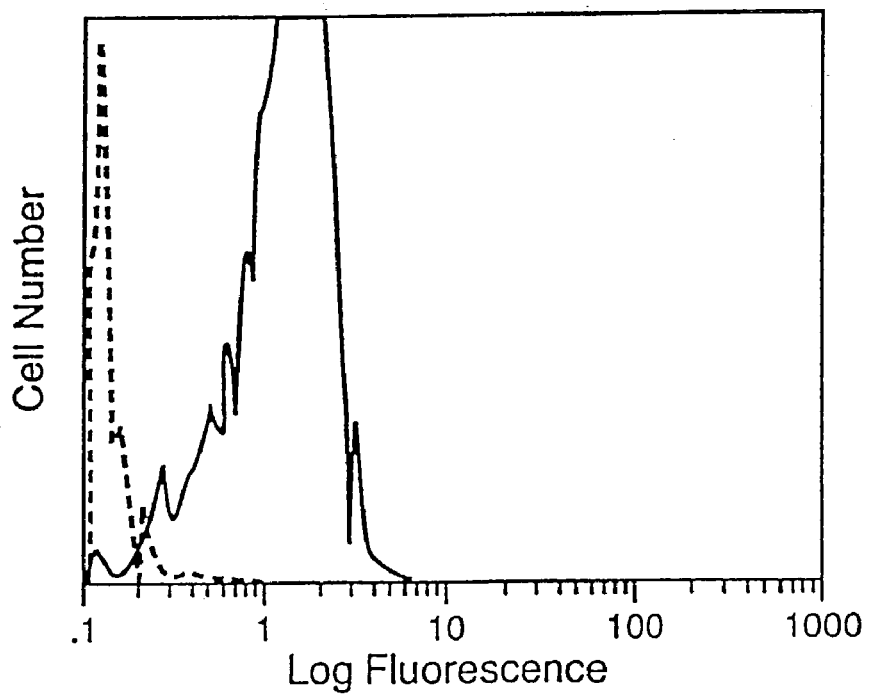

FIG. 15 shows tumor cell surface antigen expression. Expression of CD33 by HL60 cells grown at 4 weeks in a representative tumor mass in vivo as determined by indirect immunofluorescence.

Figure 16:
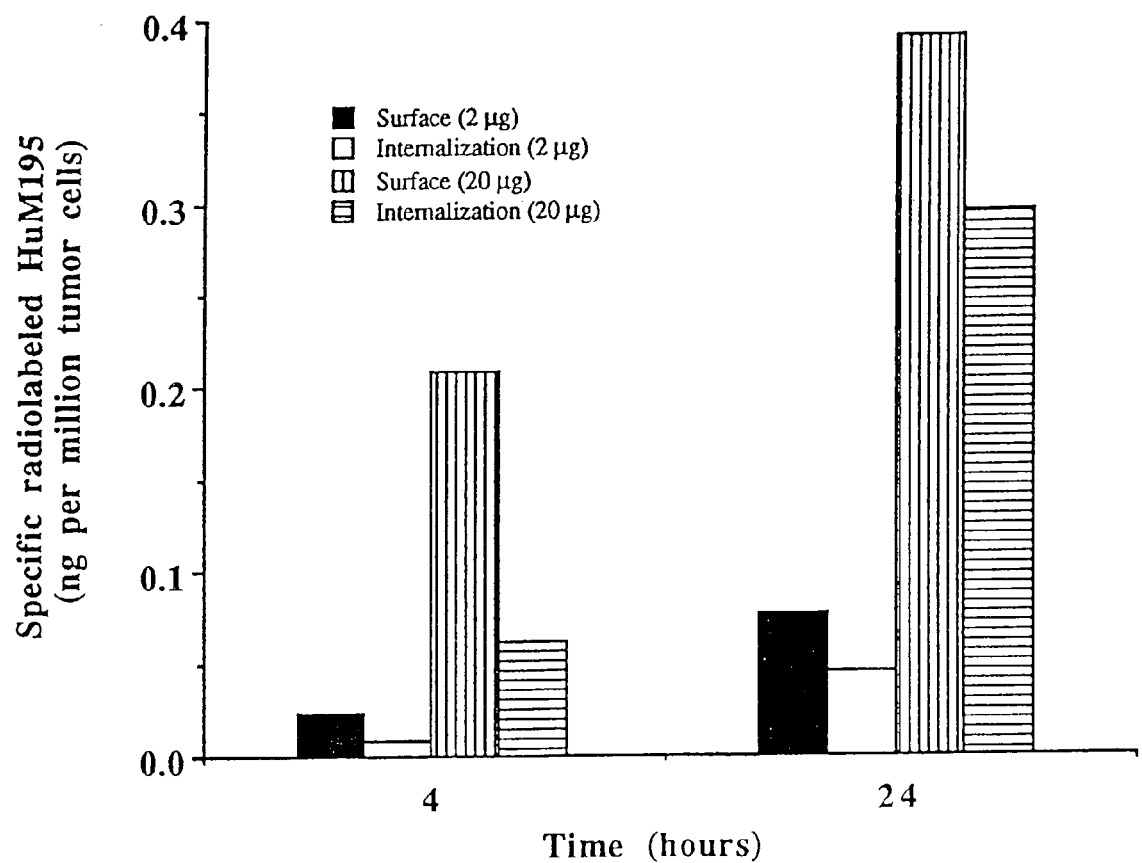

FIG. 16 shows the specific binding and internalization of $^{125}$I-HuM195 in tumors in vivo. Tumor-bearing mice at 4 weeks after transplantation received infusions of 2 or 20 µg of $^{125}$I-HuM195 shown in parenthesis. Mice were sacrificed at 4 or 24 hours after the infusion. Tumors were excised, weighed and counted. Specific surface-bound and internalized HuM195 were calculated. Standard deviation was less than 10%.

Figure 17A:
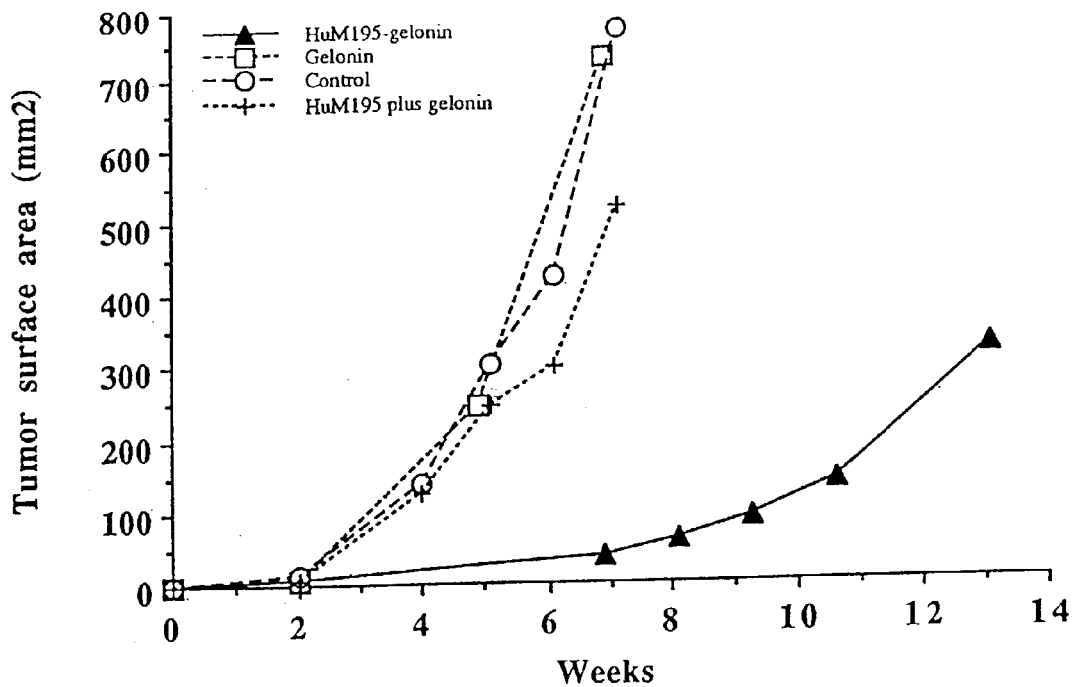
Figure 17B:
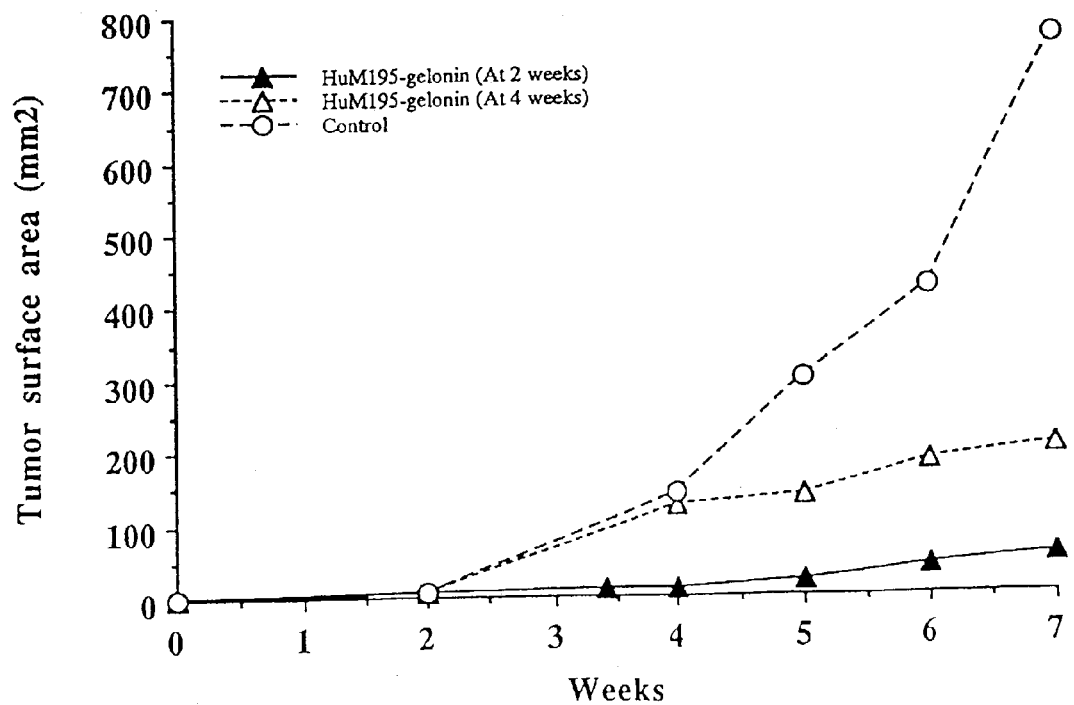

FIGS. 17A–17B show the treatment of human leukemia cells in vivo by HuM195-rGel immunotoxin. Mice were i.p. transplanted with $10^7$ HL60 human leukemia cells. FIG. 17A shows that at the tenth day, mice were treated by three injections of 100 nM: HuM195-rGel (four mice); rGel (four mice); HuM195 mixed with rGel (five mice); and control saline (five mice). At the time indicated by the x-axis, tumor surface area was measured. One of five mice in the control group and one of the five mice in the HuM195-rGel (mixed but unconjugated) died in the sixth week. FIG. 17B shows that at the $14^{th}$ or $28^{th}$ days, mice were treated with 6 injections of 100 nM: HuM195-rGel immunotoxin (four mice at the $14^{th}$ day; four mice at the $28^{th}$ day); control saline (five mice). At times indicated by the x-axis, tumor surface area was measured.

DETAILED DESCRIPTION OF THE INVENTION

As used herein, the term "chimeric antibodies" or "chimeric peptides" refer to those antibodies or antibody peptides wherein one portion of the peptide has an amino acid sequence that is derived from, or is homologous to, a corresponding sequence in an antibody or peptide derived from a first gene source, while the remaining segment of the chain(s) is homologous to corresponding sequences of another gene source. For example, a chimeric heavy chain antibody peptide may comprise a murine variable region and a human constant region. The two gene sources will typically be two separate species, but will occasionally involve one species.

Chimeric antibodies or peptides are typically produced using recombinant molecular and/or cellular techniques. In many cases, chimeric antibodies have variable regions of both light and heavy chains that mimic the variable regions of antibodies derived from one mammalian species, while the constant and/or framework portions are homologous to the sequences in antibodies derived from a second, different mammalian species.

As used herein, the definition of chimeric antibody, however, is not limited to this example. A chimeric antibody is any antibody in which either or both of the heavy or light chains are composed of combinations of sequences mimicking the sequences in antibodies of different sources, whether these sources be from differing classes, differing antigen responses, or differing species of origin, and whether or not the fusion point is at the variable/constant boundary. For example, chimeric antibodies can include antibodies where the framework and complementarity-determining regions (CDRs) are from different sources. For example, non-human CDRs are integrated into human framework regions linked to a human constant region to make "humanized antibodies." See, e.g., PCT Application Publication No. WO 87/02671; U.S. Pat. No. 4,816,567; EP Patent Application 0173494; Jones, et al., *Nature,* 321:522–525 (1986); and Verhoeyen, et al., *Science,* 239:1534–1536 (1988).

As used herein, the term "human-like framework region" is a framework region for each antibody chain, and it usually comprises at least about 70 or more amino acid residues, typically 75 to 85 or more residues. The amino acid residues of the human-like framework region are at least about 80%, preferably about 80–85%, and most preferably more than 85% homologous with those in a human immunoglobulin. This shared feature with other endergenous antibodies is useful in generating a targeting moiety which introduces only a minor immune reaction, e.g., a mechanism which minimizes response to "self" markers.

As used herein, the term "humanized" or "human-like immunoglobulin" refers to an immunoglobulin comprising a human-like framework region and a constant region that is substantially homologous to a human immunoglobulin constant region, e.g., having at least about 80% or more, preferably about 85–90% or more and most preferably about 95% or more homology. Hence, most parts of a human-like immunoglobulin, except possibly the CDRs, are substantially homologous to corresponding parts of one or more native human immunoglobulin sequences.

As used herein, the term "hybrid antibody" refers to an antibody wherein each chain is separately homologous with reference to a mammalian antibody chain, but the combination represents a novel assembly so that two different antigens are recognized by the antibody. In hybrid antibodies, one heavy and light chain pair is homologous to that found in an antibody raised against one antigen recognition feature, e.g., epitope, while the other heavy and light chain pair is homologous to a pair found in an antibody raised against another epitope. This results in the property of multi-functional valency, i.e., ability to bind at least two different epitopes simultaneously. Such hybrids may, of course, also be formed using chimeric chains. As used herein, the terms "monoclonal antibody" means an antibody composition recognizing a discrete antigen determinant. It is not intended to be limited as regards the source of the antibody or the manner in which it is made.

For this invention, an antibody or other peptide is specific for a CD33 if the antibody or peptide binds or is capable of binding CD33, e.g., protein as measured or determined by standard antibody-antigen or ligand-receptor assays, e.g., competitive assays, saturation assays, or standard immunoassays such as ELISA or RIA. This definition of specificity applies to single heavy and/or light chains, CDRs, fusion proteins or fragments of heavy and/or light chains, that are also specific for CD33 if they bind CD33 alone or if, when properly incorporated into immunoglobulin conformation with complementary variable regions and constant regions as appropriate, are then capable of binding CD33 with specificity.

In competition assays the ability of an antibody or peptide fragment to bind an antigen can be determined by detecting the ability of the peptide to compete with the binding of a compound known to bind the antigen. Numerous types of competitive assays are known and are discussed herein. Alternatively, assays that measure binding of a test compound in the absence of an inhibitor may also be used. For instance, the ability of a molecule or other compound to bind the c-erbB-2 protein can be detected by labelling the molecule of interest directly or it may be unlabelled and detected indirectly using various sandwich assay formats. Numerous types of binding assays such as competitive binding assays are known (see, e.g., U.S. Pat. Nos. 3,376,110, 4,016,043, and Harlow and Lane, *Antibodies: A Laboratory Manual,* Cold Spring Harbor Publications, N.Y. (1988)). Assays for measuring binding of a test compound to one component alone rather than using a competition assay are also available. For instance, immunoglobulins can be used to identify the presence of the CD33. Standard procedures for monoclonal antibody assays, such as ELISA, may be used. For a review of various signal producing systems which may be used see, U.S. Pat. No. 4,391,904.

Further, the specificity of the binding moieties to CD33 can be determined by their affinity. Such specificity exists if the dissociation constant ($K_D=1/K$, where K is the affinity constant) of the moiety is <1 mM, preferably <100 nM, and most preferably <1 nM. Antibody molecules will typically have a KD in the lower ranges. $K_D=[R-L]/[R][L]$ where [R], [L], and [R-L] are the concentrations at equilibrium of the receptor or CD33 (R), ligand, antibody, or peptide (L) and receptor-ligand complex (R-L), respectively. Typically, the binding interactions between ligand or peptide and receptor or antigen include reversible noncovalent associations such as electrostatic attraction, Van der Waals forces, and hydrogen bonds.

Other assay formats may involve the detection of the presence or absence of various physiological or chemical changes that result from the interaction, such as down modulation, internalization, or an increase in phosphorylation. See *Receptor-Effector Coupling—A Practical Approach,* ed. Hulme, IRL Press, Oxford (1990).

Gelonin belongs to a class of potent ribosomal-inactivating plant toxins. Other members of this class of ribosomal-inactivating plant toxins are the chains of abrin, ricin and modeccin. Gelonin, like abrin and ricin, inhibits protein synthesis by damaging the 60S sub-unit of mammalian ribosomes. Gelonin appears to be stable to chemical and physical treatment. Furthermore, gelonin itself does not bind to cells and, therefore, is non-toxic (except in high concentrations) and is safe to manipulate in the laboratory. The inactivation of ribosomes is irreversible, does not appear to involve co-factors and occurs with an efficiency which suggests that gelonin acts enzymatically.

Gelonin and ricin are among the most active toxins which inhibit protein synthesis on a protein weight basis. Gelonin is 10 to 1000 times more active in inhibiting protein synthesis than ricin A chain. Peptides like ricin and abrin are composed of two chains, an A chain which is the toxic unit and a B chain which acts by binding to cells. Unlike ricin and abrin, gelonin is composed of a single chain, and, because it lacks a B chain for binding to cells, it is itself relatively non-toxic to intact cells. As used herein, gelonin refers to the naturally occurring, purified gelonin. Recombinant gelonin, or rGel, refers to that gelonin or enzymatically active fragment of gelonin which has been cloned into an expression vector or other suitable vehicle, expressed in *Escherichia coli* or other suitable organism, and purified accordingly. Active fragments and derivatives include any compounds which have the same core structure as the full length structure of gelonin but lack the entire primary sequence. These fragments or derivatives will have the same or improved biological or cytotoxic activity as gelonin. The cytotoxicity of the gelonin fragments or derivatives may be routinely determined by those with skill in the art using the rabbit reticulocyte lysate assay.

Mammalian cells apparently lack the ability to bind and/or to internalize the native gelonin molecule. Conjugates of gelonin with monoclonal antibody, such as M195 directed to a tumor associated antigen present on certain tumor cells, provide both a specific method for binding the gelonin to the cell and a route for internalization of the gelonin-antibody complex. The M195 antibody may serve as a useful carrier of such drugs providing an efficient means of both delivery to the tumor and enhanced entry into the tumor cells themselves. In addition, specific antibody delivery of cytotoxic drugs to tumors will provide protection of sensitive sites such as the liver that do not express CD33 and bone marrow stem cells from the deleterious action of the toxin. Use of drugs conjugated to the M195 antibody as a delivery system allows lower dosage of the drug itself, since all drug moieties are conjugated to antibodies which concentrate within the tumor or leukemia.

Conjugates of the monoclonal antibody may be made using a variety of bifunctional protein coupling agents. Examples of such reagents are SPDP, iminothiolane (IT), bifunctional derivatives of imidoesters such as dimethyl adipimidate, HCl, active esters such as disuccinimidyl suberate, aldehydes such as glutaraldehyde, bis-azido compounds such as bis(p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as a 1,5-difluoro-2,4-dinitrobenzene.

Administration of the immunotoxins of the present invention to an individual who has been diagnosed as having a leukemia that is characterized by the expression of CD33 protein will allow targeting and concentration of the cytotoxic agent at the site where it is needed to kill the tumor cells. By so targeting the cytotoxic agent, non-specific toxicity to other organs, tissues and cells will be eliminated or decreased.

When used in vivo for therapy, the immunotoxins are administered to the human or animal patient in therapeutically effective amounts, i.e., amounts that eliminate or reduce the tumor burden or in amounts to eliminate residual disease after an earlier treatment with chemotherapy or radiation therapy. They will normally be administered parenterally, preferably intravenously. The dose and dosage regimen will depend upon the nature of the leukemia and its population, the characteristics of the particular immunotoxin, e.g., its therapeutic index, the patient, and the patient's history. The amount of immunotoxin administered will typically be in the range of about 0.01 to about 10.0 mg/kg of patient weight.

For parenteral administration the immunotoxins will be formulated in a unit dosage injectable form (solution, suspension, emulsion) in association with a pharmaceutically acceptable parenteral vehicle. Such vehicles are inherently non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The immunotoxin will typically be formulated in such vehicles at concentrations of about 0.1 mg/ml to 10 mg/ml.

The immunotoxins of the present invention may also be used in a method of killing tumor cells in bone marrow. In this method, the bone marrow is first removed from an individual having a neoplastic disease such as leukemia. Subsequently, the bone marrow is treated with a cytocidally effective dose of an immunotoxin of the present invention and returned to the individual.

The following examples provide a detailed description of the preparation, characterization, and use of the immunotoxins of this invention. These examples are not intended to limit the invention in any manner.

EXAMPLE 1

Purification of Gelonin

Seeds of *Gelonium multiflorum* were shelled and the nuts ground in a homogenizer with eight volumes of 0.14 M NaCl containing a 5 mM sodium phosphate (pH 7.4). The homogenate was left overnight at 4° C. with continuous stirring, cooled on ice and centrifuged at 35,000×g for 20 minutes at 0° C. The supernatant was removed, dialyzed against 5 mM sodium phosphate (pH 6.5) and concentrated using a pm10 filter. The sample was layered on a CM-52 ion-exchange column (20×1.5 cm) equilibrated with 5 mM sodium phosphate (pH 6.5). Material which bound to the ion exchange resin was eluted with 400 ml of 0 to 0.3 M linear NaCl gradient at a rate of 25 ml per hour at 4° C. Five ml fractions were collected. The fractions were monitored at 280 nm in a spectrophotometer. The gelonin eluted in about fractions 55–70 and was the last major elution peak. Fractions 55–70 were pooled, dialyzed against double distilled water and concentrated by lyophilization. The purity and the molecular weight of each preparation was checked on high pressure liquid chromatography using a TSK 3000 gel permeation column with 50 mM sodium phosphate buffer (pH 7.4) and 15% SDS-PAGE. Gelonin migrated as a single band with an approximate molecular weight of 29–30,000 daltons.

EXAMPLE 2

Construction of Recombinant Gelonin (rGel)

Recombinant gelonin (rGel) has recently been cloned and expressed in *E. coli* (Rosenblum et al., J. Interferon Cytokine Res., 15:547 (1995)). The chromatographic behavior of recombinant gelonin (~28 kD) appeared to be identical to that of native gelonin with respect to its binding and elution from both CM-52 cellulose and blue Sepharose. Functional analysis of the purified recombinant gelonin was performed using inhibition of cell-free protein synthesis in rabbit reticulocyte lysates. Purified native gelonin inhibited protein synthesis by 50% at a concentration of 406 pg/ml, whereas purified recombinant gelonin demonstrated 50% inhibition at 205 pg/ml. Thus, the purified recombinant gelonin demonstrated a two-fold greater specific activity than native gelonin. Thus, recombinant gelonin may have an advantage over native gelonin because of the lack of glycoslylation of the recombinant molecule and because fusion toxins between HuM195 and recombinant gelonin could result in a more-defined molecule that may avoid inadvertent inactivation of either the toxin or the antibody molecule during the chemical conjugation process or during subsequent reduction during storage.

EXAMPLE 3

Assay of Gelonin Activity

The gelonin activity was monitored in a cell-free protein synthesis inhibition assay. The cell-free protein synthesis inhibition assay was performed by sequentially adding to 50 ml rabbit reticulocyte lysate, mixing after each addition, the following components: 0.5 ml of 0.2 M Tris-HCl (pH 7.8), 8.9 ml of ethylene glycol, and 0.25 ml of 1 M HCl.

Twenty μl of a salt-amino acid-energy mixture (SAEM) consisting of: 0.375 M KCl, 10 mM Mg(CH$_3$CO$_2$)$_2$, 15 mM glucose, 0.25–10 mM amino acids (excluding leucine), 5 mM ATP, 1 mM GTP, 50 mM Tris-HCl (pH 7.6), 10 ml Creatinine phosphate-creatinine phosphokinase, 8 ml [$^{14}$C]-leucine (Amersham, 348 mCi mmol), and adding 1.5 ml of solutions containing varying concentrations of the gelonin mixture. The mixture was incubated for 60 minutes at 30° C. [$^{14}$C]-leucine incorporation was monitored in an aliquot of the mixture by precipitating synthesized protein on glass fiber filters, washing in 10% TCA and acetone, and monitoring the radioactivity in a Beta-counter using Aquasol scintillation fluid. Gelonin with a specific activity no lower than 4×10$^9$ U/mg was used for conjugation with the antibodies. A unit of gelonin activity is the amount of gelonin protein which causes 50% inhibition of incorporation of [$^{14}$C]-leucine into protein in the cell free assay.

EXAMPLE 4

Preparation of Murine and Humanized Monoclonal Antibody M195

Murine monoclonal antibody M195 was produced from hybridomas resulting from the fusion of NS-1 mouse myeloma cells and the spleen cells of a five week old BALB/c mouse immunized with leukemia cells from a patient with acute non-lymphocytic leukemia (FAB-M2). Supernatant fluids from cloned hybridoma cultures were screened against the panel of leukemia cell lines and the original ANLL leukemia cells using *Staphylococcus aureus* protein A (PA) erythrocyte resetting. The repeatedly subcloned M195 hybridoma was expanded in the doubly pristane-primed (C57 BL/6 times BALB/c) F1 mice. M195 was purified on a PA-Sepharose by affinity chromatography using sequential PH step dilutions. Purity was determined on SDS-polyacrylamide gels stained with coomassie brilliant blue.

Humanized monoclonal antibody M195 was prepared as described by Co et al., "Chimeric and Humanized Antibodies with Specificity for the CD33 Antigen", *J. Immunol.*, 148:1149–1154 (1992) and was produced from hybridomas and purified as above.

EXAMPLE 5

Modification of Gelonin and M195 for Conjugation

Gelonin in phosphate buffered saline was concentrated to approximately 10 mg/ml in a Centriprep 10 concentrator. Triethanolamine hydrochloride (TEA/HCl) (pH 8.0), and EDTA were added to a final concentration of 60 mM and 1 mM, respectively. A 2-iminothiolane stock solution (500 mM in 60 mM TEA/HCl buffer containing 1 mM EDTA, pH 8.0) was added to a final concentration of 1 mM and the sample was incubated for 90 min at 0.4° C. under a stream of nitrogen gas with stirring. Excess iminothiolane was removed by gel filtration on a column of Sephadex G-25 (1×24 cm) pre-equilibrated with phosphate-EDTA buffer (pH 7.5) containing 0.01 M Na$_2$HPO$_4$, 0.0018 M KH$_2$PO$_4$, 0.0034 M KCl, 0.001 M EDTA and 0.17 M NaCl. Fractions were analyzed for protein content in microtiter plates using Bio-Rad assay. Gelonin eluted at the void volume (about fractions 21–23). These fractions were pooled and stored at 4° C.

M195 linked with 4-succinimidyloxycarbonyl-α-methyl-α(2-pyridyldithio)toluene (SMPT) is prepared by coupling 2-IT-modified gelonin with SMPT-modified MAB M195. Briefly, to modify M195 with SMPT, 10 mg of antibody in 1.0 ml of PBS is diluted 1:1 with 2× borate buffer (0.05 M sodium borate 1.7% sodium chloride, pH 9.0) and 52 ml of 4 mM SMPT in dry DMF is slowly added to the antibody solution. The reaction is incubated at room temperature for 2 hr with stirring under $N_2$. Excess SMPT is removed by passing the reactions mixture through a Sephadex G-25 column containing phosphate-EDTA buffer (pH 7.5) and antibody positive fractions are evaluated by Bio-Rad assay. The fractions are pooled and stored at 4° C. under $N_2$. The cross-link with 2-IT is carried out at 27° C. under $N_2$ with stirring for 96 hrs. The final product is purified as previously described for SPDP.

EXAMPLE 6

Conjugation of SPDP-Modified Monoclonal Antibody M195 with Iminothiolane-Modified Gelonin One milligram of purified gelonin (2 mg/ml in PBS) prepared as described in Example 1 or 2 was modified with iminothiolane as described in Example 5. Monoclonal antibody M195 modified as described in Example 5 was mixed with an equal weight of the modified gelonin. This proportion corresponded to a 5-fold molar excess of gelonin as compared to antibody. The pH of the mixture was adjusted to 7.0 by the addition of 0.05 M TEA/HCl buffer (pH 8.0) and the mixture was incubated for 20 hours at 4° C. under nitrogen. Iodoacetamide (0.1 M) was added to a final concentration of 2 mM to block any remaining free sulfhydryl groups and incubation was continued for an additional hour at about 25° C. The reaction mixture was stored at 4° C. until purification by gel filtration.

EXAMPLE 7

Purification and Activity of Gelonin-Monoclonal Antibody M195 Complexes

Non-conjugated gelonin and low molecular weight products were removed from the reaction mixtures of Example 6 by gel filtration on a Sephadex S-300 column (1.6×31 cm) pre-equilibrated with PBS. Reaction mixtures from Example 6 were concentrated to approximately 1 ml with a Centricon 30 microconcentrator before loading on the Sephadex column. The column was washed with PBS. One ml fractions were collected and 50 ml aliquots are analyzed for protein by the Bradford assay. To remove unconjugated M195, the high molecular weight peak (fraction 28–40) from the S-300 column was applied to an affinity chromatography column of Blue Sepharose CL-6B (1×24 cm) pre-equilibrated with 10 mM phosphate buffer (pH 7.2) containing 0.1 M NaCl. After sample loading, the column was washed with 30 ml of buffer to completely elute non-conjugated antibody. The column was eluted with a linear salt gradient of 0.1 to 2 M Nacl in 10 mM phosphate buffer (pH 7.2). Protein content of the eluted fractions was determined by the Bradford assay.

Figure 1:
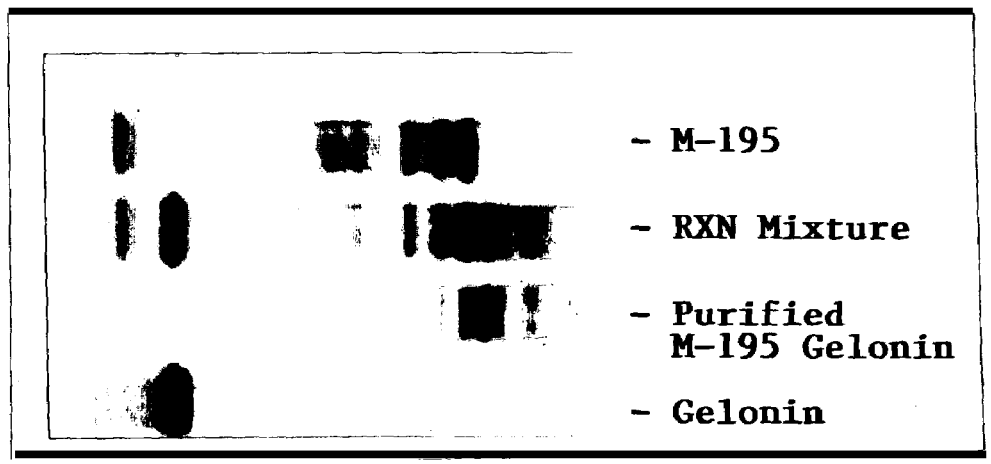
FIG. 1 shows the SDS-gel electrophoresis fractionation of M195 and the immunotoxin M195-IT under non-reducing conditions with a gradient of 5% to 20% acrylamide. Lanes.

Gelonin-conjugated antibody bound to the column and was eluted with a linear salt gradient of 0.2 to 2 M NaCl in 10 mM phosphate buffer (pH 7.2). The antibody-gelonin complex eluted at approximately 0.7 M NaCl. Protein content of the eluted fractions was determined by the Bradford assay. The protein-containing fractions were pooled and the elution pattern confirmed by electrophoresis on a 5 to 20% gradient non-reducing polyacrylamide gel. FIG. 1 illustrates the electrophoretic pattern of purified M195, an unpurified reaction mixture of M195 and gelonin, purified M195-gelonin immunotoxin or gelonin alone. The flow-through peak (fractions 14–20) contains only free antibody while fractions 50–80, eluted with high salt, contain M195-gelonin conjugate free of unconjugated gelonin or antibody.

Different batches of conjugates containing approximately one or two gelonin molecules per mAb showed no loss of binding titer as compared to unconjugated HuM195 or M195. However, a batch of HuM195 conjugated with an average of three gelonin molecules per mAb, as determined by SDS-PAGE, demonstrated a lower binding titer against both HL60 cells, as assayed by indirect flow cytometry, and AL67 cells, as assayed by ELISA. Therefore, the immunoconjugates containing fewer than three gelonin molecules per antibody maintained complete biological activity of the mAb, as measured in flow-cytometric assays, and toxin activity as measured in a rabbit reticulocyte lysate translation assay. Conjugates with more than two gelonin molecules had a decreased avidity for the antigen, which resulted in a less potent molecule. The loss of avidity may be due to steric interference with the antigen-binding site or to instability of the over-conjugated immunotoxin.

The rabbit reticulocyte in vitro translation system was utilized to estimate the gelonin activity of the essentially pure gelonin-M195 immunotoxin antibody complex. One unit of activity in this assay was defined as the amount of protein required to provide 50% inhibition of protein synthesis as compared to untreated controls. Utilizing this assay, the specific activity of both the native gelonin and the M195-gelonin conjugate were determined to be $2\times10^8$ U/mg and $8.2\times10^5$ U/mg, respectively. The essentially pure gelonin M195 antibody is active in the reticulocyte lysate assay. A 1:1000 dilution of the original sample caused approximately a 50% inhibition of protein synthesis, i.e., a 50% reduction of the incorporation of $^{14}$C-leucine into protein. Thus, the activity of the original preparation was 1000 U/ml.

EXAMPLE 8

Cytotoxicity of Immunoconjugates

With reference to FIG. 2, M195 immunotoxin was tested for its ability to kill HL60 cells in comparison to free gelonin. Inhibition of protein synthesis (using the test of a tritiated mix of amino acid (0.5 mCi/ml; New England Nuclear Corp.) incorporation into trichloroacetic acid (TCA) precipitable protein) was used as a measure of activity of the agent used. Final concentrations of the M195-gelonin immunotoxin ranged from 4 mg/ml to 5 ng/ml. Gelonin final concentrations ranged from 44 mg/ml to 0.6 mg/ml. The M195-gelonin immunotoxin was approximately 600 times more potent than the free gelonin alone. $ID_{50}$ for the M195-gelonin immunotoxin was approximately 0.4 nM. Inhibition of protein synthesis by the M195-gelonin immunotoxin subsequently leads to either lack of cell division or to cell death. Cell death was confirmed by experiments using trypan blue exclusion to determine total number of live cells and percentages of live cells.

As can be seen in FIG. 3, concentrations of the M195-gelonin immunotoxin inhibited greater than 80% of HL60 protein synthesis, while comparable concentrations of the immunotoxin had no effect on SKLY16 cells. Thus, the selectivity of the M195-gelonin immunotoxin for CD33-expressing cells is apparent.

As is seen in comparing FIGS. 4 and 5, the length of time of exposure to the immunotoxin affects its activity. In fact, an approximate ten-fold increase in potency of the M195-gelonin immunotoxin is seen after a five day incubation with HL60 cells (see FIG. 5) as opposed to a three day incubation (see FIG. 4).

With reference to FIGS. 6A–6B, the binding of humanized M195 (HuM195)-immunotoxin to HL60, U937 or MOLT4 cells were examined. HuM195 and HuM195-immunotoxin were added to HL60 cells (FIG. 6A, or U937 or MOLT4 cell lines (FIG. 6B,). FIGS. 6A–6B illustrate that the humanized M195-gelonin immunotoxin is capable of binding specifically to target cells. Using indirect flow cytometry, the humanized M195-gelonin immunotoxin showed more specific binding to CD33 positive cell lines (HL60 and U937) compared to the humanized M195 antibody alone. It did not bind to the CD33 negative cell line (MOLT4).

As illustrated in FIG. 7, the humanized M195-gelonin immunotoxin inhibited protein synthesis approximately 4500-fold over that seen with gelonin alone. FIG. 7 illustrates the ability of humanized M195-gelonin immunotoxin to kill HL60 cells, as the $ID_{50}$ was less than 10 picomoles. This $ID_{50}$ for the immunotoxin is more than 4000 times lower than the $ID_{50}$ of gelonin alone.

With reference to FIG. 8, HL60 cells were incubated for one hour on ice in the presence of the humanized M195 antibody or F79, an isotype matched control antibody. Humanized M195-gelonin immunotoxin was added at a concentration of 0.15 mg/ml. Cells were incubated 90 hours at 37° C. The quantity of live cells was determined by the trypan blue exclusion technique. The percent inhibition represents the reduction of cells killed in the presence of the competing antibody as compared to cells killed by the immunotoxin alone. As seen in FIG. 8, the humanized M195 antibody was able to block cytotoxicity of the humanized M195 antibody-gelonin immunotoxin in a dose dependent manner. In contrast, Fd79, a non-specific humanized IgG1, had no effect at the same levels.

EXAMPLE 9

In Vitro Cytotoxicity of HuM195-rGel Immunoconjugate

HuM195-rGel was tested for its ability to kill CD33 positive and CD33 negative cells in comparison to free rGel. Activity and cytotoxicity were determined by inhibition of incorporation of $^3$H-leucine into protein and by trypan blue exclusion. Dose-response curves were generated by testing the inhibitory effects of HuM195-rGel on the protein synthesis of HL60 cells (CD33 positive) and RAJI (CD33 negative) in culture (FIG. 9A). In the in vitro assays, the concentration of HuM195-rGel required to inhibit protein synthesis in HL60 cells by 50% was 0.6 nM, whereas the concentration of rGel alone required to nonspecifically inhibit protein synthesis in both HL60 and RAJI cells by 50% was about 200 nM (FIG. 9A). In the concentration range of 10–100 nM HuM195-rGel, protein synthesis in HL60 cells was almost completely inhibited, while no cytotoxicity was observed with the CD33 negative cell lines RAJI (FIG. 9A) and DAUDI. However, HuM195 alone did not affect the protein synthesis in CD33 positive HL60 cells (FIG. 9A). These results show that the inhibition of protein synthesis was due to specific binding and activity of the immunotoxin, and not a nonspecific property of the antibody itself. The specific targeting of leukemic cells by HuM195-rGel appeared to occur via the CD33 antigen binding site and not through the Fc region or other non-specific binding sites on target cells.

The cytotoxicity of HuM195-rGel was directly determined by trypan blue analysis. The concentration of HuM195-rGel required to kill 50% of cells was 0.7 nM (FIG. 9B), similar to the concentration of HuM195-rGel required to inhibit protein synthesis by 50% (FIG. 9A). However, HuM195-rGel did not kill CD33 negative RAJI cells at the highest concentration of 100 nM, suggesting that it may be used safely for study in vivo.

EXAMPLE 10

Blast Cells from AML Patients are Sensitive to the HuM195-rGel Immunoconjugate

The effect of HuM195-rGel on AML blasts in primary culture using a combination of liquid cultures and methylcellulose cultures was examined. Samples were obtained from 15 patients with newly diagnosed or relapsed AML and 1 patient with CML blast crisis. The CD33 expression measured by flow cytometry on bone marrow blasts ranged from 75.7% to 99.8%. Incubation for 24 hours in liquid culture with HuM195-rGel resulted in dose-responsive decreases in clonogenic cell recovery for each of 7 patient samples as measured by colony formation in methylcellulose-containing medium (Table I). Growth inhibition due to equimolar concentration of unconjugated HuM195 and rGel was seen only at very high concentrations ($\geq 100$ nM). The $IC_{50}$ of immunotoxin was 1 nM to 30 nM for patient samples and 0.3 nM for HL60 cells (24-hour incubation). In contrast, the $IC_{50}$ of unconjugated monoclonal antibody with rGel (a mixture of both molecules, each at the stated concentration) was 100 nM to 200 nM. Prolonging the incubation time to 72 hours had a variable effect on $IC_{50}$ for patient samples, but consistently lowered the $IC_{50}$ for unconjugated antibody and rGel.

Patient samples had varying CD33 expression, measured on bone marrow blasts by flow cytometry as the percent of cells with positive staining. While this method confirms the presence of CD33 on the cell surface, it may not give an accurate measure of receptor density. It was therefore determined whether results obtained from flow cytometry would correlate with sensitivity to the immunotoxin. FIG. 10 shows the trend of lower $IC_{50}$ with increasing CD33-positivity (r=−0.25, p=0.59).

To further evaluate the potency of HuM195-rGel with respect to log-kill, the IC90 was determined empirically for HL60 and Patient #2. The $IC_{50}$ for HL60 cells show a 4 log difference in sensitivity to HuM195-rGel versus free rGel, whereas the $IC_{90}$ shows a 2 log difference. The patient sample was more sensitive to immunotoxin than to unconjugated antibody and rGel by a factor of 25 at the $IC_{50}$ and by a factor of 9 at the $IC_{90}$. These results indicate that the degree of antibody-mediated specificity was not uniform across the dose-response range, but that there was measurable targeting at concentrations necessary for 1 log reduction in clonogenic cells during a 24 hour incubation.

TABLE I

IC50 of immunotoxin versus conjugated monoclonal antibody and toxin for HL60 and 7 AML patient samples

| | $IC_{50}$ (nM)[a] | | | |
|---|---|---|---|---|
| | 24-hour incubation[b] | | 72-hour incubation[b] | |
| | immunotoxin | HuM195 + rGel | immunotoxin | HuM195 + rGel |
| HL60 | 0.3 | >10 | 0.02 | 100 |
| Patient #1 | 1.0 | 100 | 5.0 | 20 |
| Patient #2 | 4.0 | 100 | 0.1 | 3.0 |
| Patient #3 | 6.0 | | | |
| Patient #4 | 30 | 200 | | |
| Patient #5 | 1.0 | | | |
| Patient #6 | 10 | | | |
| Patient #7 | 9 | | | |

[a]50% inhibitory concentration estimated from plot of colonies formed versus concentration of immunotoxin or unconjugated equimolar amounts of HuM195 and rGel.
[b]Cells incubated in suspension culture with immunotoxin or unconjugated molecules for time shown, then washed and plated for colony formation.

EXAMPLE 11

Cell-Surface Expression of CD33 Following In Vitro Treatment with the HuM195-rGel Immunoconjugate Measurement of CD33 expression by flow cytometry reveals a unimodal distribution within which there are individual cells with lower or higher CD33 expression. It was determined whether cells which are relatively resistant to HuM195-rGel on the basis of low CD33 expression would produce more highly expressing cells on clonal expansion or give rise to a resistant clone with stably down-regulated CD33 expression. HL60 cells were separated into CD33-bright and CD33-dim populations by FACS. CD33 expression was measured again by flow cytometry following 6 days in culture. Both populations were 100% CD33-positive with mean channel numbers of 166.7 and 166.3, respectively.

The persistence of CD33 expression was also reflected in the does-response curves of OCI/AML5 following preincubation for 0 to 6 days with immunotoxin at an inhibitory concentration. After 2, 4 or 6 days exposure to immunotoxin, OCI/AML5 continued to show sensitivity to HuM195-rGel that is stable, though not as great as that seen with naive cells (FIG. 11). Cells incubated with immunotoxin for 5 days showed only faint staining for CD33 (median fluorescence intensity 5.6 fluorescence units versus 196.1 fluorescence units in the control not treated with immunotoxin). To confirm that there was a decrease in the density of immunotoxin-binding sites, cells were then exposed to fresh immunotoxin followed by FITC-labeled anti-human-IgG. Pretreated cells agin showed decreased median fluorescence intensity (85 fluorescence units versus 498 fluorescence units in naive cells), indicating decreased immunotoxin binding. CD33 expression was restored after incubation for 5 days in immunotoxin-free media (205 fluorescence units in pretreated versus 220 fluorescence units in untreated cells). The transient decrease in CD33 positivity correlates with the unexpected time course for internalization of immunotoxin-bound CD33 molecules and expression of new CD33 on the cell surface. These results provide guidelines for the optimal timecourse of adminstration to leukemic patients of the immunotoxin of the present invention.

EXAMPLE 12

The HuM195-rGel Immunoconjugate Displays Synergy with Cryopreservation

Treatment of AML with high dose chemotherapy followed by transplantation of cryopreserved autologous bone marrow is frequently unsuccessful due to the presence of leukemic blast progenitors in the bone marrow autograft. Cryopreservation itself has some antileukemic effects, to which other purging modalities have been added. To determine whether cryopreservation would enhance the effect of HuM195-rGel against CD33 positive AML blasts, cells from 12 patient samples were resuspended in freezing medium (10% DMSO; 50% FEBS) immediately following a 24 hour exposure to HuM195-rGel (1 nM), frozen at −70° C. for a minimum of 24 hours, quickly thawed by immersion in a 37° C. water bath, washed several times and plated on methylcellulose to determine clonogenic cell recovery. The data shown in FIGS. 12A12C indicate that there is a greater than additive effect against all but one patient sample.

EXAMPLE 13

Purging Leukemic Targets from Bone Marrow and Effects of Target Cell Concentration Bone marrow aspirates were obtained form normal donors according to Memorial Sloan Kettering Cancer Center IRB protocols. Mononuclear cells were collected by Ficoll-Paque sedimentation, washed, and gamma irradiated with 8 Gy. Marrow cells were divided into aliquots in 96 well plates at a final concentration of 1×106 cells/ml. HL60 cells at a final concentration of 0.667×105 cells/ml and HuM195-gelonin immunotoxin at various concentrations were added to the plates. After a 6 day incubation at 37° C., cells were assayed for [$^3$H]-thymidine incorporation.

In order to determine the effect that cell concentration may have upon the efficacy of the HuM195-gelonin immunotoxin, HL60 cells were serially diluted and incubated in the presence of a single concentration of immunotoxin at 2 μg/ml. The immunotoxin was most effective at low cell concentrations (FIG. 13). At higher cell concentrations, the immunotoxin lost potency. This was not due to an excess of cell surface binding sites over immunotoxin molecules, as even at the highest cell concentrations, there were 100–1000 more molecules of immunotoxin than available binding sites. In other experiments, serial dilutions of the immunotoxin and gelonin were incubated with three different concentrations of HL60 cells. Both the immunotoxin and gelonin were more potent at lower cell concentrations.

The dependence of killing on cell density raised the issue of the efficacy of the immunotoxin in the presence of large numbers of non-target cells. Therefore, to determine whether the immunotoxin was able to kill HL60 cells in the presence of excess numbers of CD33 cells, HL60 cells were mixed with a 15-times excess of irradiated normal bone marrow cells. This ratio simulates that which might be found in a typical marrow in early relapse contaminated with low levels of leukemic cells. The presence of bone marrow had minimal effect upon the cytotoxicity of the immunotoxin (FIG. 14).

EXAMPLE 14

In Vivo Antitumor Effects of the HuM195-rGel Immunoconjugate

Nude mice retain limited ability to generate antibodies to the HL60 cells after transplant and that CD33 can be down-regulated by this response. Therefore, the expression of CD33 on the tumors was assessed. The cells from the leukemic tumors retained expression of CD33 positive antigen after growth in vivo, as determined by flow cytometry at saturating mAb concentrations (FIG. 15). The internalization of 125I-HuM195 into the target cells in vivo was rapid, and similar to the observations in vitro. At 4 hours after infusion of 2 or 20 μg antibody, 23–26% of bound $^{125}$1-HuM195 was internalized, whereas a higher rate of internalization (38–43%) was seen at 24 hours (FIG. 16).

The leukemic cell growth in the subcutaneous space and peritoneum of nude mice was substantially reduced by HuM195-rGel. At 10 days after transplantation of HL60 cells into the peritoneum of nude mice, tumors of about 2 mm$^3$ in size were present in the subcutaneous space (FIGS. 17A–17B). After three injections of HuM195-rGel at a dose of 36 μg per mouse beginning at 10 days, two out of four mice did not develop tumors for up to 5 months after transplantation. Tumors grew slowly in the other two immunotoxin-treated mice. Control groups of mice (treatment with saline alone, gelonin alone or HuM195 mixed with rGel at the same final concentrations) did not show significant tumor inhibition or any cures.

To assess whether activity could be observed against larger tumors, in a second trial, six injections of HuM195-rGel was also tested (twice a week for 3 weeks at the same dose of 36 μg per mouse at 14 days and 28 days after transplantation with HL60 cells). Despite the increase in the number of doses from three to six, the delay in treatment to 28 days caused less inhibition of tumor growth by HuM195- rGel (Table II and FIG. 17B). After 3 weeks of treatment with HuM195-rGel, two out of four mice had no tumors in the group treated 14 days after transplantation; however, all four mice developed local tumors when treated 28 days after transplantation. This may be due to a difficulty in delivering HuM195 to larger solid tumors or to the development of resistant cells within the larger tumors.

TABLE II

Tumor size at 7 weeks after HuM195-rGel treatment

| Groups | Control | rGel | HuM195 + rGel | HuM195-rGel | | |
|---|---|---|---|---|---|---|
| | | | | 10 days | 14 days | 28 days |
| Mouse 1 | 420 | 648 | 342 | no tumor | no tumor | 96 |
| Mouse 2 | 525 | 696 | 400 | no tumor | no tumor | 160 |
| Mouse 3 | 900 | 760 | 550 | 49 | 81 | 180 |
| Mouse 4 | 1225 | 803 | 784 | 96 | 117 | 380 |
| Mouse 5 | death | N/A | death | N/A | N/A | N/A |
| Mean | 768 | 727 | 519 | 36 | 50 | 204 |
| ±SD | 368 | 68 | 197 | 46 | 59 | 123 |

Ten million HL60 leukemia cells were transplanted ip into nude mice. Mice were treated with three injections of equimolar amounts of HuM195-rGel, rGel or HuM195 + rGel (administered together but not conjugated) beginning at 10 days after HL60 transplantation. Two other groups of mice were treated with six injections of HuM195-rGel beginning at the 14 or 28 day after HL60 transplantation. Subcutaneous tumor size (cross product in mm$^2$) at 7 weeks is shown. 'Death' indicates mice that died in the sixth week.

EXAMPLE 15

Fusion Constructs of the HuM195-rGel Immunoconjugate

The compositions of the present invention may include fusion constructs of the M195 monoclonal antibody and a cytotoxic moiety. Such fusion constructs of the immunotoxin of the present invention may be prepared by the method of Co et al..

Prior to use in these studies, the Sp2/0-Ag14 cells will be grown initially in the presence of 0.1 mg/ml of native gelonin. Over several months, the concentration of gelonin will be gradually increased until the cells can be maintained in up to 10 mg/ml. Cells will then be cloned by limiting dilution in the presence of 10 mg/ml gelonin and the resulting colonies resistant to gelonin will be expanded. Gelonin will then be removed from the culture media for two passages and the cells challenged again with gelonin exposure to confirm development of stably-resistant clones. After tests to confirm the production and activity of humanized M195, gelonin-resistant SP2/0 cell producing antibody will be grown and the cDNA for the M195 antibody removed from the total DNA by incubation with restriction endonuclease. In parallel, the cDNA from JM105 E. coli expressing optimized gelonin will be removed, purified and the DNA encoding gelonin released after digestion with HindIII and EcoRI. The gelonin gene will be ligated into the heavy-chain fragment and the insert replaced into gelonin resistant SP2/0 cells. Cells will then be sub-cloned by limiting dilution and the clones screened for both humanized antibody production and gelonin content. Finally, positive clones will be expanded and the recombinant fusion protein will be purified and tested in both in vitro cytotoxicity assays and in vivo tissue distribution, pharmacokinetics, therapeutics and toxicity trials. A comparison of M195 gelonin fusion protein properties to the characteristics of the previously described M195-gelonin constructs will be performed to determine the advantages and drawbacks of each. Based upon these studies, a Phase I clinical study of chimeric M195-gelonin fusion protein may be performed in patients with advanced breast cancer.

In conclusion, therefore, it is seen that the present invention and the embodiments disclosed herein are well adapted to carry out the objectives and obtain the ends set forth at the outset. Certain changes can be made in the method and apparatus without parting from the spirit and scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is therefore well adapted to carry out the objects and attain the ends and advantages mentioned, as well as others inherent therein.

What is claimed is:

1. A composition comprising a fusion protein between an antibody exhibiting binding specificity for CD33 protein and a gelonin toxin selected from the group consisting of gelonin, recombinant gelonin and functionally active recombinant gelonin fragments.

2. The composition of claim 1, wherein said binding specificity is for an extracellular epitope of CD33.

3. The composition of claim 1, wherein said antibody exhibiting binding specificity for CD33 protein is a single chain antibody.

4. The composition of claim 1, wherein said antibody exhibiting binding specificity for CD33 protein is selected from the group consisting of murine monoclonal antibodies, humanized monoclonal antibodies and chimeric antibodies.

5. The composition of claim 1, further comprising a pharmaceutically carrier.

6. The composition of claim 1, wherein the gelonin toxin is recombinant gelonin.

7. The composition of claim 1, wherein the gelonin toxin a functionally active recombinant gelonin fragment.

8. A method of killing tumor cells in bone marrow, wherein said tumor cells are characterized by expression of CD33 antigen protein, comprising the steps of:
    removing bone marrow from an individual having a neoplastic disease;
    contacting said bone marrow with a cytocidally effective dose of a composition comprising a conjugate of an antibody exhibiting binding specificity for CD33 protein and a gelonin toxin selected from the group consisting of gelonin, recombinant gelonin and functionally active recombinant gelonin fragments; and
    reinfusing said contacted bone marrow back into said individual.

9. The method of claim 8 further comprising the step of: freezing said contacted bone marrow prior to reinfusion thereof.

10. The method of claim 8, wherein said binding specificity is for an extracellular epitope of CD 33.

11. The method of claim 8, wherein said antibody exhibiting binding specificity for CD33 protein is a single chain antibody.

12. The method of claim 8, wherein said antibody exhibiting binding specificity for CD33 protein is selected from the group consisting of murine monoclonal antibodies, humanized monoclonal antibodies and chimeric antibodies.

13. The method of claim 8, wherein said conjugate is a fusion protein between said antibody exhibiting binding specificity for CD33 protein and a gelonin toxin selected from the group consisting of gelonin, recombinant gelonin and functionally active recombinant gelonin fragments.

14. The method of claim 8, wherein said composition further comprises a pharmaceutically carrier.

15. The method of claim 8, wherein the gelonin toxin is recombinant gelonin.

16. The method of claim 8, wherein the gelonin toxin is a functionally active recombinant gelonin fragment.

* * * * *

UNITED STATES PATENT AND TRADEMARK OFFICE
CERTIFICATE OF CORRECTION

PATENT NO. : 7,297,335 B2 Page 1 of 1
APPLICATION NO. : 10/386204
DATED : November 20, 2007
INVENTOR(S) : Michael G. Rosenblum It is certified that error appears in the above-identified patent and that said Letters Patent is hereby corrected as shown below:

In claim 7, column 18, line 37, please insert --is-- after "toxin".

In claim 9, column 18, line 52, please insert --,-- after "claim 8".

Signed and Sealed this

Eighth Day of April, 2008

JON W. DUDAS
*Director of the United States Patent and Trademark Office*